US011168183B2

(12) United States Patent
Blanchemain et al.

(10) Patent No.: US 11,168,183 B2
(45) Date of Patent: Nov. 9, 2021

(54) METHOD FOR THE PRODUCTION OF HYDROGEL COMPRISING CHITOSAN AND NEGATIVELY CHARGED POLYELECTROLYTES, AND CELLULAR, POROUS MATERIAL RESULTING FROM SAID HYDROGEL

(71) Applicants: UNIVERSITE DE LILLE, Lille (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); CENTRE HOSPITALIER REGIONAL UNIVERSITAIRE DE LILLE, Lille (FR)

(72) Inventors: Nicolas Blanchemain, Merville (FR); Bernard Martel, Nieppe (FR); Claudia Flores, Lille (FR); Frédéric Cazaux, Marchiennes (FR); Feng Chai, Loos (FR); Nicolas Tabary, Lille (FR); Marco Lopez Heredia, Valenciennes (FR)

(73) Assignees: UNIVERSITE DE LILLE, Lille (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); CENTRE HOSPITALIER REGIONAL UNIVERSITAIRE DE LILLE, Lille (FR)

( * ) Notice: Subject to any disclaimer, the term of this patent is extended or adjusted under 35 U.S.C. 154(b) by 481 days.

(21) Appl. No.: 15/740,414

(22) PCT Filed: Jul. 1, 2016

(86) PCT No.: PCT/FR2016/051684
§ 371 (c)(1),
(2) Date: Jan. 18, 2018

(87) PCT Pub. No.: WO2017/001808
PCT Pub. Date: Jan. 5, 2017

(65) Prior Publication Data
US 2018/0186939 A1    Jul. 5, 2018

(30) Foreign Application Priority Data
Jul. 2, 2015 (FR) ..................................... 15 56283

(51) Int. Cl.
*A61K 31/722* (2006.01)
*C08J 3/075* (2006.01)
*C08J 3/05* (2006.01)
*A61L 26/00* (2006.01)
*A61L 27/52* (2006.01)
*A61M 3/00* (2006.01)
(Continued)

(52) U.S. Cl.
CPC .............. *C08J 3/075* (2013.01); *A61L 26/008* (2013.01); *A61L 27/52* (2013.01); *A61M 3/005* (2013.01);
(Continued)

(58) Field of Classification Search
CPC .. A61L 26/008; A61L 27/52; C08J 2205/022; C08J 2305/08; C08J 2405/08
See application file for complete search history.

(56) References Cited

U.S. PATENT DOCUMENTS

| 6,039,470 | A | 3/2000 | Conwell |
| 6,344,488 | B1 * | 2/2002 | Chenite ................ A61K 9/0019 |
| | | | 514/777 |

(Continued)

FOREIGN PATENT DOCUMENTS

| CN | 102125516 A | 7/2011 |
| CN | 102516739 A | 6/2012 |

(Continued)

OTHER PUBLICATIONS

Chinese Office Action issued in corresponding Chinese Patent Application No. 201680050794 X dated Mar. 2, 2020 and Search Report (with English Translation), 12 pages.
(Continued)

*Primary Examiner* — Michael A Salvitti
(74) *Attorney, Agent, or Firm* — MH2 Technology Law Group LLP

(57) ABSTRACT

The present invention concerns a method for producing a hydrogel comprising the following steps in succession:
  a first step (i) of providing at least one powder of an anionic polymer (A) and at least one chitosan powder (B) comprising amine functions ($-NH_2$);
  a second step (ii) consisting in dry mixing at least the powders (A) and (B) from the first step in order to form a mixture of powders;
  a third step (iii) of suspending the mixture of powders obtained from the second step in an aqueous medium having a pH that can enable the anionic polymer (A) to be dissolved without dissolving the chitosan (B);
  a fourth step (iv) of adding an acid to the suspension obtained from the third step in order to form the hydrogel; or
  the third (iii) and fourth (iv) steps are replaced by a mixing fifth step (v), comprising mixing an acidified aqueous medium including at least one compound (C) comprising at least one unit of a hexose or a unit derived from a hexose, and/or at least one phosphate of said compound (C), with said mixture comprising at least the powders (A) and (B) obtained from the second step (ii).

17 Claims, 4 Drawing Sheets

(51) Int. Cl.
*B01J 13/00* (2006.01)
*C08J 9/00* (2006.01)
*C08J 9/28* (2006.01)

(52) U.S. Cl.
CPC ....... *B01J 13/0056* (2013.01); *B01J 13/0069* (2013.01); *C08J 3/05* (2013.01); *C08J 9/0066* (2013.01); *C08J 9/28* (2013.01); *C08J 2205/022* (2013.01); *C08J 2305/08* (2013.01); *C08J 2305/16* (2013.01); *C08J 2405/08* (2013.01); *C08J 2405/16* (2013.01)

(56) References Cited

U.S. PATENT DOCUMENTS

| | | | | |
|---|---|---|---|---|
| 8,703,924 | B2* | 4/2014 | Andersson | A61K 9/1652 536/20 |
| 8,906,403 | B2* | 12/2014 | Martel | A61L 27/34 424/424 |
| 9,180,166 | B2* | 11/2015 | Arinzeh | A61L 27/26 |
| 9,205,103 | B2* | 12/2015 | Portela Da Gama | A61L 27/56 |
| 10,449,257 | B2* | 10/2019 | Hauser | A61K 38/07 |
| 10,583,222 | B2* | 3/2020 | Cazalbou | A61F 2/2846 |
| 10,612,001 | B2* | 4/2020 | Hazot | A61L 27/225 |
| 2008/0254094 | A1* | 10/2008 | Martel | A61L 29/146 424/424 |
| 2010/0316715 | A1* | 12/2010 | Andersson | A61L 27/20 424/484 |
| 2011/0028431 | A1* | 2/2011 | Zerbe | A61P 11/06 514/58 |
| 2011/0229970 | A1* | 9/2011 | Ma | C12N 5/0654 435/455 |
| 2011/0274742 | A1* | 11/2011 | Arinzeh | A61K 35/28 424/443 |
| 2013/0045242 | A1* | 2/2013 | Portela Da Gama | A61L 27/20 424/400 |
| 2013/0196915 | A1* | 8/2013 | Wang | A61K 38/27 514/11.4 |
| 2013/0216592 | A1* | 8/2013 | Delair | C08L 5/02 424/400 |
| 2014/0044969 | A1* | 2/2014 | Chane-Ching | C01G 25/006 428/402 |
| 2014/0349933 | A1* | 11/2014 | Hauser | A61K 35/51 514/9.1 |
| 2015/0216894 | A1* | 8/2015 | McCarthy | A61K 9/70 514/55 |
| 2018/0186939 | A1* | 7/2018 | Blanchemain | A61M 3/005 |
| 2019/0167714 | A1* | 6/2019 | Brown | A61K 9/0041 |

FOREIGN PATENT DOCUMENTS

| | | |
|---|---|---|
| FR | 2903594 A | 1/2008 |
| WO | 9907416 A1 | 2/1999 |
| WO | 2011070529 A2 | 6/2011 |
| WO | 2013015688 A1 | 1/2013 |
| WO | 2015120085 A1 | 8/2015 |

OTHER PUBLICATIONS

International Preliminary Report on Patentability issued in corresponding International Patent Application No. PCT/FR2016/051684 dated Jan. 2, 2018, 17 pages.
International Search Report and Written Opinion issued in corresponding International Patent Application No. PCT/FR2016/051684 dated Nov. 23, 2016, 22 pages.
Patois et al., "Novel thermosensitive chitosan hydrogels: In vivo evaluation", Journal of Biomedical Materials Research Part A, vol. 91A, No. 2, Nov. 1, 2009 (Nov. 1, 2009), pp. 324-330.
Chinese Office Action issued in corresponding Chinese Patent Application No. 201680050794.X dated Nov. 20, 2020 and Search Report, (with English language translation) 19 pages.

* cited by examiner

FIG.1A
FIG.1B
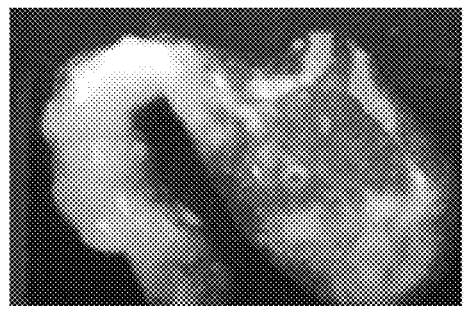
FIG.2A
FIG.2B

METHOD FOR THE PRODUCTION OF HYDROGEL COMPRISING CHITOSAN AND NEGATIVELY CHARGED POLYELECTROLYTES, AND CELLULAR, POROUS MATERIAL RESULTING FROM SAID HYDROGEL

The present disclosure relates to the technical field of methods of producing hydrogels, in particular implantable hydrogels, as well as to the technical field of methods of producing cellular materials obtained via said hydrogels, in particular relating to the technical field of methods of producing physical hydrogels.

The present disclosure also relates to the technical field of hydrogels, cellular materials (in particular sponges) obtained from said hydrogels, and medical devices comprising such hydrogels or cellular materials.

BACKGROUND

Hydrogels or macromolecular gels usually comprising mainly water are matrices of polymers expanded by a large quantity of water. The macromolecules are interconnected, forming a network constituting a scaffold that provides the gel with the properties of a material with viscoelastic properties.

The bonds between polymer chains may have two forms: permanent or reversible. When they are permanent, the covalent bonds are observed to be present; these are known as chemical hydrogels. When the bonds between the chains are reversible, the macromolecules interact via non-covalent bonds of the hydrogen, ionic or hydrophobic type, or dipole-dipole type; these are known as physical hydrogels.

Hydrogels may be used as biomaterials, i.e. as medical devices, in particular implantable devices. Such hydrogels may comprise a polymer network based on natural polysaccharides (for example: starch, cellulose, carrageenans, alginates, etc.), proteins (gelatine), or based on synthetic polymers such as polyacrylamides, polyacrylates ("carbomers"), forming entangled three-dimensional macromolecular networks that are stabilized by covalent bonds (irreversible or permanent chemical gels) or by hydrogen bonds, hydrophobic bonds, dipolar bonds (dipole-dipole), or electrostatic bonds (reversible physical gels).

Chitosan (CHT), which belongs to the family of naturally available polysaccharides, is the only cationic polymer of natural origin that is currently known (positively charged polyelectrolyte, denoted as $PE^+$); it is produced by deacetylation of chitin, or is extracted directly from fungi. Chitosan is a copolymer composed of the randomly distributed β-1,4-linked D-glucosamine and N-acetyl-D-glucosamine. A chitosan is characterized by its degree of deacetylation, which represents the percentage of glucosamine repeat units on its macromolecular chain.

Chitin is the component of the exoskeleton of arthropods (crustaceans) or the endoskeleton of cephalopods. Chitosan is characterized by its high amine function content (of the order of 5 millimoles (mmol) per gram, depending on its degree of deacetylation (routinely in the range 60% to 90%). CHT is used a great deal in biomedical applications for its properties of biocompatibility, bio-resorbability, haemocompatibility, healing properties, and for its action against the development of bacterial strains.

Chitosan is a polymer that is available in the form of a powder or as flakes with a variety of grain sizes. It is only the natural amine polymer that is in the form of a powder, which is insoluble in pure water, but soluble as soon as the water is acidified with a minimum of 1% (vol/vol) of concentrated acetic acid. Other polyamines carrying primary amine functions (—$NH_2$) exist, such as polyvinylamine, polyallylamine, and polyethyleneimine, but they are only available in the state of concentrated aqueous solutions or solids in the form of a gum (because they are highly hydroscopic), and they do not constitute powders that have fluidity or that flow freely.

The cross-linking of CHT by an ionic route to obtain a hydrogel is a mild method that is easy to carry out because it takes place spontaneously, without heat or a catalyst. Thus, anionic cross-linking agents are used with sulfates, citrates, phosphates or polyphosphates, polyoxyanions, or calcium salts. The method consists of immersing the CHT "article" (film, monolith, etc.) in an aqueous solution containing the cross-linking agent that diffuses into the "article" at the same time as water, which causes it to swell and form a gel. Alternative methods consist of adding the cross-linking agent to an aqueous solution of chitosan that has been dissolved in a dilute acetic acid solution (often containing at least 0.5% of acetic acid, for example) or, in contrast, the solution of CHT is added drop by drop to the solution of cross-linking agent using a syringe, for example (J. Berger et al./European Journal of Pharmaceutics and Biopharmaceutics 57 (2004) 19-34).

Cyclodextrins, which also belong to the polysaccharide family, are cage molecules that are capable of forming reversible inclusion complexes with many active principles, in particular lipophiles. Cyclodextrins are cyclic polysaccharides obtained from an enzymatic degradation of starch. They are constituted by a concatenation of six to eight α-(1,4)-linked glucopyranose units forming a macrocycle with a periphery that is rich in hydroxyl functions, making them soluble in water, while the interior forms an apolar, hydrophobic cavity that provides cyclodextrins with complexing properties with lipophilic active principles by forming inclusion complexes. Chemical gels (non-reversible) are known that are based on cyclodextrins obtained by cross-linking a cyclodextrin with epichlorhydin, a diepoxide, a diisocyanate, pyromellitic dianhydride, sodium trimetaphosphate, or EDTA used as cross-linking agents. These cross-linked or "hyperbranched" cyclodextrin polymers form either insoluble macroscopic gels or soluble nanogels that have trapping and vectoring properties for organic molecules, including therapeutic agents (Progress in Polymer Science, Volume 38, Issue 2, February 2013, Pages 344-368, Advanced Drug Delivery Review 65 (2013) 1188-1203; Belstein Journal of Organic Chemistry, 2014, 10, 2586-2593).

Previous studies combining cyclodextrin and chitosan have been published. However, those studies did not consist of obtaining a macroscopic physical gel from a mixture of a cyclodextrin polymer and chitosan. As an example, Auzely (C. R. Chimie 14 (2011) 167-177), firstly covalently grafted cyclodextrin (CD) onto chitosan (=CHT-CD), and secondly grafted adamantane (ada) onto chitosan (=CHT-ada). Once mixed into solution, those two polymers form a supramolecular macroscopic gel by forming a network formed by those two types of polymers, caused by the spontaneous formation of inclusion complexes between the cyclodextrins and the adamantane, forming a hydrogel stabilized by supramolecular type interactions between the interpenetrating networks of CHT-ada and CHT-CD. In addition, the very high stability of the CD-ada complex does not allow a third molecule such as a therapeutic agent to enter the inclusion mixtures in the cavities of the cyclodextrins if the stoichiometry (or the molar ratio) of CD/ada is less than 1, because all of the cavities are irreversibly complexed with an adamantane group.

The majority of gels sold as medical devices are ready for use, i.e. already hydrated, and they contain a mineral filler, for example calcium phosphate or beta tricalcium phosphate, or an active therapeutic molecule. In'oss™, an injectable gel based on HPMC (hydroxypropylmethylcellulose) containing hydroxyapatite, may be mentioned in respect of bone grafting; or Periochip® or Atridox®, based on gelatine and PLA polymer (polylactic acid), respectively containing an active principle for an application in periodontology, may also be mentioned. Gels also exist for filling wrinkles that are based on hyaluronic acid or collagen, and there also exist coats of gels on a textile panel based on CMC (carboxymethylcellulose), optionally filled with an active principle, used to produce dressings that act to maintain the hydration of a wound or to release an active principle. Biom'Up markets a bone graft material (Matribone®) in the form of a sponge based on collagen including a beta tricalcium phosphate powder filler.

Physical hydrogels formed by an ionic complex resulting from interactions between a negative polyelectrolyte and a positive polyelectrolyte also exist. The publication by the "International Journal of Biological Macromolecules" and entitled "Recent development of chitosan-based polyelectrolyte complexes with natural polysaccharides for drug delivery" the authors of which are Yangchao Luo and Qin Wang, 64 (2014) 353-367, lists the various studies that have been carried out with chitosan over the past ten years in order to form such ionic complexes. The polyanions mixed with the chitosan are hyaluronic acid (HA), pectin, carrageenan, xanthan gum, gellan gum, cashew gum, gum arabic, carboxymethylcellulose, glucomannan, and kondagogu gum.

The hydrogels formed from such polyelectrolyte complexes also acquire their hydrogel form via physical interactions with a lower energy, such as a dipole-dipole association, Van der Waals bonds and hydrogen bonds. Compared with hydrogels obtained by chemical cross-linking, the hydrogels formed by ionic complexes have the advantage of not being toxic, of being tolerated well by living organisms, and of being biocompatible. Specifically, chemical cross-linking agents may induce a certain amount of toxicity deriving from the reactive functional groups that they support. In order to eliminate any trace of them in the gel, steps for purifying implantable gels for medical use, in general by washing with water or with solvents, are thus necessary for hydrogels that are cross-linked chemically. However, such steps could degrade the structure of those hydrogels. Furthermore, when such chemically cross-linked hydrogels include an active principle, those steps purifying the hydrogels formed could cause a loss of active principle by diffusion into the medium that serves to extract the traces of cross-linking agent.

Physical gels (reversible) can be destroyed by raising temperature, by increasing ionic strength or by varying the polarity of the solvent or of the pH, while chemical gels are definitively stabilized by the covalent bonds.

The publication entitled "Chitosan/cyclodextrin nanoparticles as macromolecular drug delivery system", by A. H. Krauland and M. J. Alonso, International Journal of Pharmaceutics 340 (2007) 134-142, describes the synthesis of nanoparticles presented as nanogels based on chitosan and a carboxymethylated β-cyclodextrin monomer that can slowly release encapsulated molecules. Nanogels are then obtained rather than gels in the macroscopic state. A nanogel may be defined as an "article" of strongly hydrated globular form, with a size that is often in the range from 20 nanometers (nm) to several hundred nm.

The publication entitled "Chemically cross-linked and grafted cyclodextrin hydrogels: from nanostructures to drug-eluting medical devices", by A. Concheiro, C. Alvarez-Lorenzo, Advanced Drug Reviews 65 (2013) 1188-1203, describes the production of hydrogels based on cyclodextrins that are chemically grafted onto preformed macromolecules (often of the poly(acrylic) type), obtained by polymerizing monomers carrying cyclodextrin, or cross-linked with cross-linking agents such as a diepoxide, a diisocyanate, pyromellitic dianhydride, sodium trimetaphosphate, or EDTA.

The publication "Chitosan derivatives bearing cyclodextrin cavities as novel adsorbent matrices", by M. Prabaharan and J. F. Mano, in Carbohydrate Polymers 63 (2006) 153-156, describes the synthesis of macromolecules of chitosan onto which cyclodextrins are grafted via amide bonds.

The active agents incorporated in physical hydrogels are molecules of high molecular weight (proteins, peptides, DNA, etc.) and delivered in controlled manner because they diffuse slowly through the network of macromolecules of polyelectrolyte complexes. The delivery of these active agents is also directly linked to the rate of erosion or of bio-resorption of the matrix of the hydrogel.

In contrast, molecules of low molecular weight diffuse rapidly through the polymer network of the gel. In fact, if the bioactive molecules have no particular interactions with the polymer or polymers forming the architecture of the gel, their low steric hindrance means that they can diffuse freely through the lattices of these very open macromolecular networks (a hydrogel being mainly composed of water), and thus the release kinetics for these small molecules is not controlled by the rate of diffusion, nor by the rate of erosion of the hydrogel, and is very rapid.

Known physical hydrogels and their corresponding cellular materials disintegrate over the short term (after a few hours) or even spontaneously when they are immersed in water, in particular when the water is charged with salts; this applies to all physiological fluids. This final characteristic is important as regards hydrogels that are intended to be implanted in the body, so that they retain their structures for a predetermined period, not only to ensure that they carry out their filling function and/or reinforcing function, but also to allow controlled and targeted release of one or more active principle(s).

Finally, there is currently no hydrogel that is capable of sequestrating or of containing a mineral filler on an implantation site (for example a bone defect); this is because degradation of the hydrogel structure is too rapid, which causes the mineral filler to be released from the matrix of the hydrogel in the short term. The mineral filler is selected from materials used for bone grafting containing calcium phosphates in various forms (powders, monolytes, granules, etc), hydroxyapatite or calcium phosphate with a constitution similar to the principal mineral constituent of bone. Specifically, incorporating a sufficient quantity of mineral filler into a hydrogel and maintaining it on the implantation site for a sufficiently long period are necessary in many applications in the field of dental surgery, maxillofacial surgery or indeed in the field of orthopaedic surgery. However, incorporating a large quantity of mineral filler into a cross-linked hydrogel physically destabilizes it and facilitates its disintegration.

US 2010/0221303 A1 and WO 2012/028620 are also known; they concern the formation of a cellular material from a polysaccharide polymer.

The present disclosure thus seeks to propose a hydrogel, in particular a physically cross-linked hydrogel, resulting from a complex of at least one negative polyelectrolyte and at least one positive polyelectrolyte in order to permit complexing of therapeutic molecules with low molecular weight (less than or equal to approximately 250 grams per mole (g/mol)), and then to ensure their slow release.

The present disclosure also seeks to propose a hydrogel that can be used to encapsulate and control the release of one or more component(s) of high molecular weight, in particular more than approximately 250 g/mol.

The present disclosure also seeks to propose a hydrogel that is compact, moldable, homogeneous, and thixotropic hydrogel (so that it can be injected).

Furthermore, the present disclosure seeks to propose a hydrogel and a cellular material obtained from said hydrogel that are stable, that do not disintegrate spontaneously when immersed in water or in a physiological medium, and that nevertheless comprise a large quantity of a mineral filler.

The present disclosure seeks to propose a hydrogel and a cellular material obtained from said hydrogel that are capable of including a large quantity of mineral filler, in particular that represents up to 90% of the mass of the device, while retaining excellent consistency, good malleability, and excellent absorption properties as regards biological fluids (blood), which can trigger the biological process of cellular differentiation leading to the genesis of osteoblast cells.

SUMMARY

The present disclosure mitigates the above-mentioned problems in that in a first aspect, it provides a method of producing a hydrogel, comprising the following steps in succession:
  a first step (i) for providing at least one powder of an anionic polymer (A) and at least one chitosan powder (B) comprising amine functions ($—NH_2$);
  a second step (ii) consisting of dry mixing at least the powders (A) and (B) from the first step in order to form a mixture of powders;
  a third step (iii) for suspending the mixture of powders obtained from the second step in an aqueous medium, in particular with stirring, having a pH that can enable the anionic polymer (A) to be dissolved without dissolving the chitosan, for example at a pH greater than or equal to 4, at a pH greater than or equal to 4.5, or even greater than or equal to 5; for example, the aqueous medium is water (for example, distilled water or ultrapure water) or an aqueous suspension of at least one living cell, such as human or animal cells, in particular stem cells, for which the pH is approximately 7 (±0.5), corresponding to the pH of a culture medium or of a physiological liquid;
  a fourth step (iv) for adding an acid to the suspension obtained from the third step in order to form the hydrogel; or
  the third (iii) and fourth (iv) steps are replaced by a fifth step (v) for mixing, comprising mixing an acidified aqueous medium comprising at least one compound (C) comprising at least one unit of a hexose or a unit derived from a hexose, and/or at least one phosphate of said compound (C), with said mixture comprising at least the powders (A) and (B) obtained from the second step (ii).

The inventors have discovered that the gelling process is strictly linked to the chemical nature of the two polymers (A) and (B), and to the particular manner in which they are employed.

The chitosan powder (constituted by glusosamine monomers and N-acetyl glucosamine units) is insoluble in an aqueous medium having a pH greater than or equal to 4, greater than or equal to 4.5, in particular greater than or equal to 5. In contrast, chitosan dissolves in an aqueous medium if it contains a dilute acid such as hydrochloric acid, acetic acid, or lactic acid. In an aqueous solution that is sufficiently acidic, the amine functions $—NH_2$ of the chitosan are protonated into ammonium functions $—NH_3^+$; because of this property, chitosan is considered to be a polycation in the context of the present disclosure (polyelectrolyte: $PE^+$).

The publication "Chitin and chitosan: Properties and applications", Ms. Rinaudo, Prog. Polym. Sci. 31 (2006) 603-632, describes the dissolution of chitosan, which depends in particular on its degree of deacetylation, its molar mass, and the pH of the aqueous medium in which the chitosan is dissolved.

It should be noted that at a pH less than or equal to 5 and greater than or equal to 4, the amine functions of the chitosan (B) will be partially protonated, but not in a sufficient quantity to dissolve the chitosan (B). Rinaudo reports that chitosan generally dissolves when the degree of ionization of the glucosamine units is greater than 0.5 (or 50%).

The proportion of ionized glucosamine units (corresponding to the degree of ionization of the chitosan) may be evaluated by acid-base quantitative analysis or by standard colloidal titration, both well known to the person skilled in the art.

Suspending the mixture of powders comprising the powders (A) and (B) in an aqueous medium brings about a reduction in the pH of this medium when the polyanion (A) includes acid functions (for example carboxylic, $—COOH$), and then the pH rises and stabilizes. However, it has been observed that when the pH of the aqueous medium, before adding the mixture of powders, is greater than or equal to 4, greater than or equal to 4.5, or even greater than or equal to 5, any drop in pH following addition of the mixture of powders is not sufficient to cause the chitosan to dissolve. Only the addition of acid in the fourth step causes a sufficient reduction in the pH to enable the chitosan to be dissolved.

The anionic polymer of the disclosure, or polyanion, is soluble at a pH greater than or equal to 4, in particular greater than or equal to 4.5, especially greater than or equal to 5, and carries functions, in particular acid sulfate functions ($—O—S(=O)_2—OH$ or $—SO_4H$) and/or their salts, or sulfonic acid functions ($—S(=O)_2—OH$ or $—SO_3H$) and/or their salts, and/or phosphoric acid functions ($—O—P(=O)_2—OH$ or $—PO_4H$) and/or their salts, and/or carboxylic acid functions ($—COOH$) and/or their salts, which are capable of forming anionic functions in an aqueous medium, in particular by releasing a proton $H^+$, namely sulfonic acid, acid sulfates, phosphoric acids, or carboxylic acids, for the formation of carboxylate functions ($—COO^-$) and/or sulfate functions $—SO_4^-$ and/or sulfonate functions $—SO_3^-$ and/or phosphonate functions $—PO_4^-$.

The macromolecules carrying the above-defined acid functions and amine functions are ionizable and are termed polyelectrolytes. Strong polyelectrolytes are distinguished from weak polyelectrolytes as a function of the propensity that these functions have to be ionized in an aqueous solution, which depends on the pKa of each polyelectrolyte. The equilibrium constant Ka is of the type $(AH) \rightleftharpoons (A^-)+$ (H$^+$), (the arrows in opposite directions indicating an equilibrated reaction), and so Ka=([A$^-$]×[H$^+$])/[H$^+$] thus, the pKa is defined as −log(Ka), which can be used to evaluate the ionization of an acid as a function of the pH of the medium. Thus, the "Polymer Handbook", 2 volume set, 4th Edition, classifies polyelectrolytes into strong and weak polyelectrolytes as a function of the pKa of the ionizable functions they carry. The acid sulfate groups, sulfonic acid groups and phosphoric acid groups are strong polyelectrolytes, i.e. ionized at a low pH (less than 2), while polyelectrolytes carrying carboxylic groups are polyanions that are classed as weak polyelectrolytes (because they are ionized at a pH that is often more than 4). The polyelectrolytes carrying primary, secondary, and tertiary amines are polycations that are classed as weak polyelectrolytes because they are ionized at a pH of less than 5 (approximately).

A complex of polyelectrolytes is formed by electrostatic interactions between the acidic and basic ionic functions. Thus, the most favorable pH conditions for the formation of a complex of polyelectrolytes are those where the pH of the solution is higher than the pKa of the polyanion, and lower than the pKa of the functions of the polycation.

Thus, in the context of the present disclosure, the term "anionic polymer" or "polyanion" means any polymer in the form of a powder comprising anionic functions or that is capable of forming anionic functions once dissolved in an aqueous medium, in particular at a pH that is greater than or equal to 4, more particularly at a pH greater than or equal to 4.5, especially at a pH greater than or equal to 5.

During the second step, the powders of chitosan (B) (PE$^+$) and of anionic polymer (PE$^-$) (A) are intimately mixed. Thus, the particles of PE$^+$ combine with particles of PE$^-$ by electrostatic interactions. These electrostatic interactions are explained by the fact that the chitosan and the anionic polymer have zeta potentials of opposite signs.

The zeta potential of chitosan may be of the order of +20 millivolts (mV) to +50 mV, and the zeta potential of the preferred cyclodextrin polymer (A1) of the disclosure, described below, is of the order of −30 mV.

During the third step (iii), the chitosan, which has not dissolved, may remain in suspension in the aqueous medium due to the presence of the highly hydrophilic PE$^-$ that remains adsorbed on its surface by electrostatic interactions, thereby forming a hydrophilic layer that can maintain a homogeneous suspension.

The term "homogeneous suspension" should be understood to mean a suspension that does not sediment out rapidly when stirring is slowed down or interrupted.

The term "powder" should be understood to mean any solid substance reduced to small grains at ambient temperature.

The term "ambient temperature" should be understood to mean a temperature in the range 10° C. to 35° C., in particular in the range 15° C. to 25° C.

The pH values indicated in the present text were measured using a pH meter at ambient temperature.

The term "polymer" as used in the context of the disclosure should in particular be understood to mean the anionic polymer and the cationic polymer of the disclosure (chitosan (B)), an oligomer or a polymer that may be a homopolymer or a copolymer (i.e. comprising at least two different repeat units).

The term "without dissolving the chitosan" should be understood to mean that none of the amine functions of the chitosan or an insufficient number of amine functions of the chitosan is protonated in the aqueous medium in order to cause the chitosan powder to dissolve. Preferably, the chitosan (B) is dissolved for a degree of alpha ionization of at least 0.5, i.e. at least 50% by number of the amine glucose units of the chitosan (B) relative to the total number of amine glucose units of chitosan (B) are ionized into glucosammonium units.

The degree of protonation to be obtained for dissolution to occur also depends on the molar mass and on the degree of deacetylation (DDA) of the chitosan: if the DDA is low, more amine functions have to be protonated than when it is high.

The degree of deacetylation of the chitosan (B) of the disclosure may be 60% or more, 75% or more, particularly 95% or less, 90% or less, in particular 85% or less.

The acid added during the fourth step (iv) or during step (v) of the method of the disclosure is different from the polyanion.

When the acid is being added, the pH of the suspension reduces, in particular to a pH less than or equal to 5, more particularly less than or equal to 4.5, in particular less than or equal to 4 s, which causes the chitosan to dissolve by protonation of its amines (—NH$_2$) into ammonium functions (—NH$_3^+$), with the acetate group (CH$_3$COO$^-$) or chloride (Cl$^-$) as the counter-ion, if the acid added is respectively acetic acid and hydrochloric acid. The chitosan macromolecules unfold under the effect of intra-molecular electrostatic repulsions between the ammonium groups formed (electrostatic charges with the same sign repel) and attain a "twisted" conformation that then occupies the entire volume of the aqueous medium. Simultaneously, ionic bonds are formed between the ammonium groups of the chitosan (—NH$_3^+$) and the anionic functions (COO$^-$) of the anionic polymer.

Next, once the amine functions have been protonated, the pH of the hydrogel rises to stabilize it, to a pH greater than or equal to 4, to a pH greater than or equal to 4.5, in particular to a pH greater than or equal to 5.

Said anionic polymer is then dispersed in the network of the chitosan. These ionic interactions cause physical cross-linking of the gel and the aqueous dispersion solidifies.

The hydrogel of the disclosure may be a macroscopic gel that has the characteristics of a viscoelastic material with a self-sustaining shape.

The characteristics relating to the pH of the acidified aqueous medium following the fourth step (iv) may also be applicable to the aqueous medium of step (v) (including a compound (C) as defined in the present text).

The term "hydrogel" as used in the present disclosure should be understood to mean a solid viscoelastic material with a self-sustaining shape, i.e. it retains the dimensions and shape of the container in which is formed after being removed from the container (for several hours or several days depending upon the conditions in which it is placed).

The first step and/or the second step and/or the third step and/or the fourth step and/or the fifth step (v) of the disclosure may be carried out at ambient temperature.

It has been observed that adding acid after the taking up into suspension of the third step is very important since this implementation means that a very firm, stable hydrogel can be obtained that can remain in a specific zone without flowing for several hours at ambient temperature or at approximately 37° C., in particular for at least 48 hours (h).

Furthermore, the hydrogel of the disclosure retains its shape and its integrity in aqueous medium, in particular at ambient temperature or at approximately 37° C., for several hours, for at least 24 h, for example, for at least 48 h.

In the prior art, physical hydrogels based on chitosan are produced by mixing the acidic aqueous solution of chitosan with the aqueous solution of polyanion or by sprinkling the polyanion, for example carboxymethylcellulose, onto the aqueous acidic solution of chitosan (pH of the order of 2-3). In both pathways, the hydrogels obtained are not as firm and stable as the hydrogel of the disclosure.

The chitosan in the hydrogel of the disclosure acts to ensure the architecture of the gel and to endow it with the required rheological properties.

The ratio of the total weight of water in grams (g) in the hydrogel relative to the total weight of hydrogel may be 50% or more, 60% or more, 70% or more, in particular 80% or more, even 85% or more, in particular 90% or more.

The hydrogel of the disclosure may be capable of having one or more properties, including the following: of being biocompatible, of being injectable using a syringe, of being capable of retaining a specific shape obtained by molding for several hours at least and/or of not flowing so that it remains in place on the zone onto which it has been applied, and of being capable of releasing one or more active substance(s).

The hydrogel of the disclosure may be thixotropic, which means that it can be injected. The hydrogel thus has a rheofluidifying behavior: the polymer fluidifies when it is exposed to a mechanical shear stress, and recovers its gel state when it is at rest, free from any stress. When the hydrogel is placed in the cylinder of the syringe, it fluidifies under the effect of the shear stress applied via the piston and can pass through the outlet orifice of the syringe then into the needle, and then possibly into a catheter, and finally it can recover its firm hydrogel form once it is free from stress on the zone onto which it is applied.

By way of example, a standard needle in fluid communication with the outlet orifice of a syringe has a diameter in the range 0.1 millimeter (mm) to 0.5 mm.

The hydrogels of the disclosure may be used in numerous medical applications, and in particular as a filler material in corrective surgery, cosmetic surgery, in urology, in dental surgery, in ophthalmology, in orthopaedics, or in maxillo-facial surgery in order to prevent the adhesion of tissues and/or to promote the generation of various types of soft tissue or bone and/or to release one or more active substance(s) over the zone onto which they have been applied.

When the hydrogels of the disclosure include at least one functional agent and/or living cells, they contribute, for example, to healing, to the treatment of a disease (cancer), to reducing pain (anaesthetic effect), to reducing inflammation, or to preventing or controlling an infection.

During the third step (iii), the aqueous medium may also include at least one compound (C) comprising at least one unit of a hexose or a unit derived from a hexose and/or at least one phosphate of said compound (C).

The term "a compound (C) comprising at least one unit of a hexose or a unit derived from a hexose" as used in the present disclosure means any compound (C) comprising at least one unit with empirical formula $C_6H_{12}O_6$ or derived from said empirical formula. It may, for example, be a hexose, or a first hexose bonded via a glycoside bond to a second hexose, which may be identical or different to the first hexose (or at least one unit derived from a hexose).

Said compound comprising at least one unit of a hexose or a unit derived from a hexose may be selected from the list comprising glucose (in the L or D form), maltose (in the L or D form), saccharose, mannose (in the L or D form), fructose (in the L or D form), lactose (in the L or D form), or a mixture thereof; for example, said compound is glucose (in the L or D form).

In the context of the present text, the term "phosphate of compound (C)" means any compound comprising at least one unit with empirical formula $C_6H_{12}O_6$ or derived from said empirical formula supporting a phosphate group (for example the phosphoryl group ($PO_3^{2-}$)) on at least one of its carbons. It may, for example, be a hexose phosphate, or a first hexose (phosphate) bonded via a glycoside bond to a second hexose (phosphate) that may be identical or different to the first hexose (phosphate) (being a unit derived from a hexose (phosphate)).

In particular, the phosphates of the compound (C) are hexose-n-phosphates or derivatives of hexose-n-phosphates (n being one of the carbon atoms numbered from 1 to 6 of the hexose unit or of the derivative of the hexose unit supporting a phosphate group).

A phosphate of compound (C) may be selected from glucose-n-phosphate (in the L or D form), in particular glucose-6-phosphate or glucose-1-phosphate; maltose-n-phosphate; saccharose phosphate; mannose-n-phosphate; fructose-n-phosphate, lactose-n-phosphate, or a mixture thereof; for example, said compound is glucose-n-phosphate (in the L or D form).

The compound (C) or the phosphate of said compound (C) may include at most 10 hexose units or units derived from hexose, in particular at most 5 hexose units or units derived from hexose, in particular one or two hexose units or hexose derivatives.

It has been observed, surprisingly, that it is possible to mix the mixture comprising at least the powders (A) and (B) obtained from step (ii) with an acidified aqueous medium without it being necessary to pass through the suspension step (iii) when said acidified aqueous medium includes at least one compound (C) comprising at least one unit of a hexose or a unit derived from a hexose and/or a phosphate of said compound (C).

This provision leads to the formation of a hydrogel that is firm and stable, even only one hour after injecting it into a culture medium, for example DMEM.

It has also been observed that the presence of the component (C) based on hexose in the aqueous medium, and thus in the end in the hydrogel, can also significantly increase the pH of the aqueous medium, in particular to a pH close to 6, and thus very substantially improve the cytocompatibility measured in vitro.

The inventors have also discovered, surprisingly, that a compound based on hexose or phosphate of hexose in the acidified aqueous medium can be used to improve the formation of a gel based on chitosan and a polyanion. The use of glucose phosphate is known as a gelling agent in order to improve the stability of solutions based on chitosan, but not to improve the formation of ionic hydrogels based on chitosan (see European journal of Pharmaceutics and Biopharmaceutics 88 (2014) 361-373).

In an implementation, the suspension of the mixture of powders obtained from the third step is cast or injected into a mold, then acid is added so as to correspondingly mold it and form the hydrogel.

In an implementation, the second step of mixing the powders (A) and (B) is carried out using a device for mixing powders, in particular a planetary stirrer, especially without milling (i.e. without significantly reducing the size of the solid particles constituting the powder).

In a variation, the aqueous medium, whether it is in step (iii) or in step (v), includes at least 0.1% by weight, for example, at least 0.5% by weight, or even at least 1% by weight, in particular at least 2% by weight, more particularly at least 3% by weight, yet more particularly at least 4% by weight, especially at least 5% by weight, of at least one compound (C) comprising at least one unit of a hexose or a unit derived from a hexose, and/or at least one phosphate of said compound (C), relative to the total volume of said aqueous medium.

In a variation, powder (A) and/or powder (B) in the first step and/or the mixture of powders comprising at least the powders (A) and (B) in the second step is/are sieved through a sieve with a mesh the size of which is less than or equal to 500 micrometers (µm), for example, less than or equal to 300 µm, or even less than or equal to 200 µm, in particular less than or equal to 150 µm, more particularly less than or equal to 125 µm.

The size distribution of the particles of the powder (A) and/or the powder (B) or of the mixture of powders (A) and (B) may be measured using a Mastersizer S (Malvern Instruments, Orsay, France) using a 300 mm lens. The sample is dispersed in the dry state with compressed air at 4 bar.

The powder (A) and/or the powder (B) and/or the mixture of powders (A) and (B), for example, in combination with at least one powder that differs from powders (A) and (B), such as at least one mineral filler, may be sieved on the sieving device with the following reference: Plastic Sieve, Nylon DIN 41p5, No: 948414 W: 0.125 µm, sold by Bioblock Scientific.

Complying with a predetermined size for the particles of polycation or polyanion is important, because it means that a gel can be formed that is homogeneous, i.e. without the presence of lumps, and with the expected viscoelastic properties.

Powder (A) and powder (B) may also be sieved with the aid of a vibrating sieve, for example those sold by Fritsch.

During the first step, the powder (A) and/or the powder (B) may be milled separately prior to passing them through a sieve, for example, with the aid of a Pulverisette 14® machine sold by Fritsch and provided with a 200 µm sieve.

In a variation, the mixture of the second step is produced by dry co-milling at least the powders (A) and (B).

The powders (A) and (B) may be dry co-milled manually in a mortar.

The powders (A) and (B) may also be co-milled in a bead mill such as a Pulverisette planetary micro-mill sold by Fritsch, in particular.

Milling can reduce the size of the solid particles and form smaller fragments. The term "co-milling" makes reference to the simultaneous milling of at least two different powders (A) and (B). In the above variations, it has been observed that co-milling and/or milling followed by mixing can reduce the size of the solid particles of the powders, and can also provide intimate mixing between the powders (A) and (B) and thus a better contact surface area between the anionic polymer and the chitosan. This provision promotes the homogeneity of the aqueous dispersion including these powders in the third step. The reproducibility in the formation of the hydrogel is thus also increased, as is the reactivity between the anionic polymer and the chitosan, in particular for solidification of the hydrogel.

In a variation, the anionic polymer comprises acid sulfate functions (—O—S(=O)$_2$—OH or —SO$_4$H) and/or salts of said acid sulfate functions, and/or sulfonic acid functions (—S(=O)$_2$—OH or —SO$_3$H) and/or salts of said sulfonic acid functions, and/or phosphoric acid functions (—O—P(=O)$_2$—OH or —PO$_3$H) and/or salts of said phosphoric acid functions, and/or carboxylic acid functions (—COOH) and/or salts of said carboxylic acid functions, for example, phosphoric acid functions and/or salts of said phosphoric acid functions; and/or carboxylic acid functions (—COOH) and/or salts of said carboxylic acid functions, or even carboxylic acid functions (—COOH) and/or salts of said carboxylic acid functions, in particular carboxylic acid functions (—COOH).

The sulfonic acid salts (sulfonate salts —SO$_3$X), acid sulfate salts (sulfate salts —SO$_4$X), phosphoric acid salts (phosphonate salts —PO$_4$X) and carboxylic acid salts (carboxylate salts —COOX) are monovalent, said salts then comprising at least one —OX group (replacing the OH group present in the acids), in which X may be selected from sodium, potassium, lithium, and silver; or even potassium or sodium.

In a variation, the anionic polymer is selected from the list comprising: a cyclodextrin polymer, hyaluronic acid, carboxymethylcellulose, heparin, a heparinate salt, especially sodium heparinate, polyacrylic acid, sodium polyacrylate, a polyacrylic acid salt, pectin, alginic acid, sodium alginate, carrageenan, xanthan gum, gellan gum (carboxylic acid salt), glucomannan, kondagogu gum, gum arabic, cashew gum, for example, from the list constituted by a cyclodextrin polymer, hyaluronic acid, carboxymethylcellulose, heparin, pectin, alginic acid, sodium alginate, acrylic acid and an acrylic acid salt, or even a cyclodextrin polymer, acrylic acid, pectin, and sodium alginate.

Heparin, a heparinate salt, and carrageenan comprise acid sulfate functions or salts of basic sulfate functions.

Hyaluronic acid, pectin, the polymer of acrylic acid or its salt, carboxymethylcellulose, alginic acid, xanthan gum, gellan gum, glucomannan, kondagogu gum, gum arabic, cashew gum and cyclodextrin polymer (depending on its mode of synthesis) comprise carboxylic acid functions (—COOH) or salts of said carboxylic acid functions (which salts are defined in the present text in the above paragraph referring to the anionic polymer).

In a variation, the anionic polymer (A) is a cyclodextrin polymer obtained by a polymerization reaction of a mixture comprising at least one cyclodextrin and/or at least one cyclodextrin derivative and/or at least one inclusion complex of cyclodextrin and/or at least one inclusion complex of a cyclodextrin derivative, with
    at least one (poly)carboxylic acid and/or its corresponding (poly)carboxylic acid anhydride (list A1); or
    at least one pyrophosphate (list A2); or
    at least epichlorhydrin, the polymer obtained undergoing a step of carboxyalkylation, in particular carboxymethylation, in a manner such as to graft carboxylic acid functions (—COOH) (list A3).

The hydrophilic network of the cyclodextrin polymer may increase the biocompatibility and ensures cohesion of the hydrogel that cannot dissolve spontaneously in the physiological medium and migrate. The hydrophilic network also provides the inclusion complex between the guest and the cavity of the cyclodextrin with stability. The cyclodextrin also contributes to the stability of the gel by improving its adsorption properties (termed reservoir properties) regulated by the host-guest affinity, and causing it to be released with a longer or shorter delay.

The hydrogel may comprise a soluble cyclodextrin polymer or an insoluble cyclodextrin polymer or a mixture thereof, for example, a soluble cyclodextrin polymer, more particularly belonging to the family (A1).

The anionic cyclodextrin polymer ensures both cross-linking of the chitosan by ionic interactions, and at the same time ensures complexing of therapeutic molecules of low molecular weight (less than approximately 250 g/mol) by the formation of inclusion complexes, and then ensures they are released slowly.

The cyclodextrin polymer of the disclosure, in particular cross-linked or hyperbranched, especially from the list (A1), may exist in the soluble or insoluble form. The soluble polymer is constituted by gels with nanometric dimensions (i.e. having dimensions that are less than or equal to approximately 100 nm) (see the publication Green Chemistry, 2015, 17, 2444-2454, which shows photographs of globular nanogels based on a cyclodextrin polymer), which form clear solutions in water. The insoluble polymer corresponds to micrometric particles (i.e. with dimensions of more than 1 μm), millimetric and beyond, which form two-phase systems in water; the solutions are thus cloudy and not clear.

The cyclodextrin polymer may be that belonging to the list (A1). This family of polymers (A1) has the advantage of being easier to take up into suspension in an aqueous medium, because these polymers are highly hydrophilic. This provision thus facilitates the formation of a homogeneous and firm hydrogel.

The cyclodextrin polymer, in particular those belonging to the list (A1), may preserve its function of retention and controlled release of molecules, in particular of small size, which is not possible with chitosan. The chitosan is complementary, because large molecules can be retained within its three-dimensional macromolecular network, and then released in a manner that is delayed to a greater or lesser extent.

Cyclodextrin polymers other than those in the list (A1) defined above also exist, however they are highly specific because their very high carboxylate function levels (at least 3 millimoles (mmol) of COOH groups per gram, in particular approximately at least 3-5 mmol of COOH groups per gram) cannot be obtained using other routes to polymerization or the chemical modification of polymers of cyclodextrins. The family of polymers in above-defined list (A1) may be used to obtain hydrogels with a self-sustaining shape, i.e. that can be molded, cut, with a firm texture, and that are homogeneous and durable.

The cyclodextrin polymer, in particular belonging to the list (A1), may be obtained from a basic mixture in which the ratio of the weight (g) of cyclodextrin(s) and/or cyclodextrin derivative(s) and/or cyclodextrin (derivative(s)) inclusion complex(es) relative to the total weight (g) of said basic mixture is 40% or more, or even 65% or more).

The term "cyclodextrin" means any native cyclodextrin, in particular α-cyclodextrin or β-cyclodextrin or gamma-cyclodextrin.

The term "cyclodextrin derivative", means any native cyclodextrin, in particular α-cyclodextrin or β-cyclodextrin or gamma-cyclodextrin, for which at least one hydroxy group, for example at least half of the hydroxy groups, is/are substituted, in particular amine-substituted, in particular with an amine function (—NH$_2$), esterified, etherified, alkylated, hydroxyalkylated, carboxyalkylated, in particular carboxymethylated, sulfoalkylated, in particular sulfobutylated, and mixtures thereof.

Said at least one hydroxy group of the cyclodextrin may be substituted with an alkyl chain, which may be linear and/or branched, unsaturated or saturated, substituted or unsubstituted, containing 1 to 10 carbon atoms, for example, 1 to 6 carbon atoms, even 1 to 4 carbon atoms, especially a methyl group, an ethyl group, a n-propyl group, an isopropyl group, a n-butyl group, an iso-butyl group, a sec-butyl group, a tert-butyl group, each of said groups, optionally and independently of each other, being substituted with one or more hydroxy groups (—OH); and/or substituted with one or more carboxylic acid groups (—COOH); and/or substituted with one or more sulfonic acid groups and/or one or more salts of said sulfonic acid functions. Said at least one hydroxy group of the cyclodextrin may thus be substituted with a hydroxypropyl group or with a carboxymethyl group.

The term "inclusion complex of cyclodextrin" or "inclusion complex of a cyclodextrin derivative", means any cyclodextrin or cyclodextrin derivative within the meaning of the present disclosure complexing a functional agent as defined in the present text, or complexing a living cell as defined in the present text.

The person skilled in the art can select one or more cyclodextrin(s) and/or one or more cyclodextrin derivative(s) and/or one or more cyclodextrin (derivatives) inclusion complex(es) that are capable of reacting with the cross-linking agent. Particularly with regard to the list (A1) of cyclodextrin polymers, if one or more of the cyclodextrin derivatives is/are used, it/they must have sufficient hydroxy groups (—OH) to be capable of carrying out a polycondensation reaction with the (poly)carboxylic acids and/or their corresponding anhydrides.

EP 1 165 621 B1 describes the synthesis of cyclodextrin polymers obtained by polycondensation reactions between (poly)carboxylic acids and native cyclodextrins (alpha, beta, gamma) or derivatives (methyl, hydroxypropyl cyclodextrins) that are ideally suited to the implementation of the disclosure. The polymer obtained is either soluble in water or insoluble, depending on the progress of the polycondensation reaction. It is characterized by a high cyclodextrin content, in the range 40% to 65% by weight, and by the richness in carboxylic acid functions, of the order of 3-5 mmol per gram of cyclodextrin polymer.

In the context of the present disclosure, the term "carboxylic acid" means an acid including a —COOH function. In the context of the present disclosure, the term "polycarboxylic acid" means an acid including at least two —COOH functions, and "its corresponding anhydride" means an acid including at least one function —CO—O—CO—.

The term "pyrophosphate" means any compound including a P—O—P linkage, in particular including the following function: —O—PO(OH)—O—PO(OH)—O—.

In an implementation, the cyclodextrin polymer obtained by reaction with epichlorhydrin does not include carboxylic acid functions, so that it undergoes a carboxyalkylation reaction, in particular carboxymethylation with the aid of chloroacetic acid in order to graft the —CH$_2$COOH groups onto said polymer.

The carboxyalkylation may be carried out with a (poly) carboxylic acid substituted with at least one atom of chlorine, bromine, or iodine onto the alkyl chain. The alkyl chain may be linear and/or branched, unsaturated or saturated, substituted or unsubstituted, containing 1 to 10 carbon atoms, for example, 1 to 6 carbon atoms, or even 1 to 4 carbon atoms, especially a methyl group, an ethyl group, a n-propyl group, an isopropyl group, a n-butyl group, an iso-butyl group, a sec-butyl group, or a tert-butyl group.

In a variation, the pyrophosphate (A2) is sodium trimetaphosphate.

In a variation, the (poly)carboxylic acid or its corresponding acid anhydride is selected from the list comprising: saturated or unsaturated or aromatic, linear or branched or cyclic (poly)carboxylic acids and hydroxypoly(carboxylic) acids, for example, from the list comprising: citric acid, polyacrylic acid, poly(methacrylic) acid, 1,2,3,4-butanetetracarboxylic acid (BTCA), maleic acid, citraconic acid, itaconic acid, 1,2,3-propanetricarboxylic acid, trans-aconitic acid, all-cis-1,2,3,4-cyclopentanetetracarboxylic acid, mellitic acid, pyromellitic acid, editic acid (ethylene diamine tetraacetic acid or EDTA), oxydisuccinic acid, thiodisuccinic acid, or from the acid anhydrides of said (poly) carboxylic acids mentioned above, such as pyromellitic dianhydride, and mixtures thereof, for example, citric acid and BTCA.

The (poly)carboxylic acid may be selected from acyclic acids, possibly not containing amine functions (—$NH_2$), more particularly from nitrogen-free acids. The cyclodextrin polymers obtained with these acids are more hydrophilic than those obtained with cyclic acids and can be synthesized by an aqueous process in contrast, for example, to polymers obtained with pyromellitic dianhydride the synthesis of which has to be carried out in DMF (dimethylformamide).

In a variation, the acid added to the suspension during the fourth step or used to acidify the aqueous medium during step (v) of the method of the disclosure is selected from the list comprising: acetic acid, in particular glacial acetic acid, formic acid, tartaric acid, salicylic acid, glutamic acid, propanoic acid, hydrochloric acid, citric acid, lactic acid, and a mixture thereof; for example acetic acid, hydrochloric acid, lactic acid and a mixture thereof, even acetic acid and hydrochloric acid.

Said acetic acid may be at least 50% concentrated, more preferably at least 80%, more preferably at least 95%, especially at least 99% ("pure" acetic acid, known as "glacial" acetic acid)

In general, at least 0.5%, or even at least 1% by volume of an acid may be added to the aqueous medium in step (iii) or in step (v) relative to the total volume of said aqueous medium.

In a subordinate variation, the acid added to the suspension during the fourth step (iv) or step (v) of the method of the disclosure is selected from hydrochloric acid, acetic acid, and lactic acid, for example, from lactic acid and hydrochloric acid, in particular lactic acid.

It has been observed that the firmness and stability of the injected hydrogel rope are better with these acids, in particular with lactic acid.

In addition, hydrochloric and lactic acids have the advantage of being odorless, compared with acetic acid.

It has also been observed that hydrochloric acid, acetic acid, and lactic acid, in particular lactic acid, especially when they are combined with at least one compound comprising at least one unit of a hexose or at least one unit derived from a hexose in the aqueous medium, can be used to obtain good results in terms of cytocompatibility in vitro (MC3T3 test cells).

The lactic acid added may be an aqueous solution comprising at least 85% by weight of pure lactic acid relative to the volume of said aqueous solution.

In a variation, the anionic cyclodextrin polymer (A) comprises at least 2 millimoles per gram (mmoles/g) of carboxylic acid functions (—COOH), for example, at least 3 mmoles/g of carboxylic acid functions (—COOH), or even at least 3.5 mmoles/g of carboxylic acid functions (—COOH).

The quantity of carboxylic functions per g of cyclodextrin polymer may be measured by acid-base titration in the presence of colored indicators.

The measurement method consists of dissolving a predetermined quantity of a cyclodextrin polymer in a given volume of water in the presence of a colored indicator, for example phenolphthalein (a few drops), then gradually adding to said solution (drop by drop), in particular using a graduated tube, a 0.1 moles per liter (mol/liter) solution of sodium hydroxide, with stirring (using a magnetic bar, for example) until the solution containing the colored indicator changes color. The number of moles of sodium hydroxide added then corresponds to the number of moles of carboxylic acid functions (—COOH) neutralized.

In a variation, the ratio of the weight (g) of said at least one chitosan powder (B) relative to the total weight (g) of hydrogel obtained from the fourth step (iv) or obtained from the fifth step (v) is 1% or more, 8% or more, 5% or more, or even 4% or more.

In a variation, the ratio of the weight (g) of said at least one anionic polymer powder (A) relative to the total weight (g) of hydrogel obtained from the fourth step (v) or obtained from the fifth step (v) is 1% or more, 20% or more, 15% or less, even 10% or less, for example, 6% or less.

In a variation, the ratio of the weight (g) of the chitosan powder (b) to the weight (g) of the polyanion powder (A) is in the range 0.6 to 1.4, in the range 0.8 to 1.2, or even in the range 0.9 to 1.1.

In a variation, the method of producing a hydrogel of the disclosure comprises adding at least one mineral filler in the form of a powder to the mixture of powders produced during the second step; for example, the ratio of the weight (g) of mineral filler relative to the total weight (g) of the mixture of powders is 30% or more. Said at least one mineral filler is thus intimately mixed with the powders (A) and (B).

Said mineral filler may be sieved and/or (co)milled in accordance with the above-defined variations regarding powders (A) and (B), in particular regarding the size of the sieved particles.

In a variation, said at least one mineral filler is selected from the list comprising: bioceramics, in particular calcium phosphates, such as hydroxyapatite and calcium betatriphosphate, calcium carbonate, alumina ($Al_2O_3$), zirconia ($ZrO_2$), glasses, glass ionomers, titanium dioxide, and a mixture thereof (for bone reconstruction).

In a variation, the aqueous medium in step (iii) or step (v) comprises at least one functional agent and/or at least one living cell.

In particular, said functional agent is a bioactive agent, more particularly a molecule, a macromolecule, or a microorganism that has a therapeutic activity. This definition also applies in the remainder of the present text.

Said functional agent may be selected from a first list (I) comprising anticoagulants, anti-thrombogenics, antimitotic agents, anti-proliferation agents, anti-adhesion agents, anti-migration agents, cell adhesion promoters, growth factors, antiparasitic agents, anti-inflammatories, vitamins, hormones, proteins, antifungals, antimicrobial molecules, antiseptics, antibiotics (especially ciprofloxacin and chlorhexidine), nicotine, one or more essential oils, and a mixture thereof; and said at least one living cell is selected from a second list (II) comprising animal cells and/or human cells and/or plant cells.

The living cells may comprise prokaryotic cells, eukaryotic cells, bacteria, yeast, plant cells, animal cells such as endothelial cells, nerve cells, lymphoblasts, fibroblasts, osteoblasts, hepatocytes, stem cells, embryo cells, adipocytes, etc.; and cells designed to express a particular molecule.

In a second aspect, the present disclosure also provides a method of producing a cellular material, in particular a sponge material, such as a sponge, comprising a method of producing a hydrogel described in any of the above variations given with reference to a first aspect of the disclosure, in order to obtain the hydrogel, and also comprising a freeze drying step carried out on the hydrogel obtained from the fourth step (iv) or from step (v) in order to form a cellular material.

The freeze drying step may be a step that can dry out a hydrated compound by freezing followed by sublimation of the ice under a reduced atmosphere.

In a variation, a pore-forming agent in powder form is added to the mixture of powders during the second step (ii) of the hydrogel production method.

A pore-forming agent of this type may be any agent that is capable of being transformed into gas under acidic conditions, with a pH less than or equal to 5, the pores of which being formed by molecules of carbon dioxide which escape from the hydrogel. Pore-forming agents like this may be ammonium carbonate, ammonium bicarbonate, sodium carbonate, sodium bicarbonate, calcium carbonate, and mixtures thereof. The proportion by weight of pore-forming agent is in the range 1% to 15% relative to the total weight of the mixture of powders in the second step. These compounds are available from Sigma-Aldrich.

In the prior art, the cellular material is designated a "porous scaffold".

The concentration of pore-forming agent affects the size of the pores in the cellular material. The mean pore size in the cellular material may be greater than or equal to 1 μm and less than or equal to 1000 μm, more preferably in the range 100 μm to 500 μm. The pore density is in the range 4% to 75%.

The porous cellular material may be flexible and elastic, i.e. it can be compressed or stretched manually in all directions without being damaged (in particular without tearing), and then tends to regain its initial dimensions (or close to its initial dimensions) after releasing the compression or stretch.

The cellular material may include closed pores.

The cellular material may have a spongy structure, such as that of a foam.

This freeze drying step may be carried out with any equipment that is known in the art. Freeze drying is carried out for a sufficient time to remove at least 98% of the water, at least 99% of the water, for example, at least 99.5% of the water.

This freeze drying step may be carried out after producing the hydrogel with a predetermined shape, for example by placing said hydrogel in a mold, then causing it to undergo a prior freezing step.

In a variation, the method of producing a cellular material comprises a heat treatment step of treating said cellular material at a temperature greater than or equal to 100° C. for at least 5 minutes, in particular for at least 60 minutes, for example, at a temperature greater than or equal to 120° C. for at least 5 minutes, in particular for at least 30 minutes, more for example, at a temperature greater than or equal to 140° C. for at least 5 minutes.

This heat treatment step is carried out on the cellular material that is obtained, in particular after the freeze drying step.

This provision very significantly improves the mechanical properties of the cellular material and its elasticity and behavior in aqueous media, in particular by reducing its dissolution rate.

It has been observed that the compressive strength may also be improved. Under the effect of a compressive stress exerted manually, the cellular material is compressed but tends to regain its initial dimensions and shape rapidly once that stress has been released. Such a quality has been observed for the dry cellular material, but also said cellular material has been impregnated with water.

In a variation, said method includes a step for impregnation of said cellular material with a solution comprising at least one functional agent and/or at least one living cell.

In particular, said functional agent is a bioactive agent.

Said functional agent may be selected from a first list (I) comprising anticoagulants, anti-thrombogenics, antimitotics, anti-proliferation agents, anti-adhesion agents, anti-migration agents, cellular adhesion promoters, growth factors, antiparasitic molecules, anti-inflammatory agents, vitamins, hormones, proteins, antifungals, antimicrobial molecules, antiseptics, antibiotics (especially ciprofloxacin and chlorhexidine), nicotine, one or more essential oils, and a mixture thereof; and said at least one living cell is selected from a second list (II) comprising animal cells and/or human cells and/or plant cells.

The living cells may comprise prokaryotic cells, eukaryotic cells, bacteria, yeasts, plant cells, animal cells such as endothelial cells, nerve cells, lymphoblasts, fibroblasts, osteoblasts, hepatocytes, stem cells, embryo cells, adipocytes etc.; and cells designed to express a particular molecule.

In a third aspect, the present disclosure provides a device for absorbing and/or draining and/or releasing a functional agent and/or for supporting at least one living cell, the device comprising:
the hydrogel obtained by carrying out the method described in accordance with any one of the variations with reference to the first aspect of the disclosure; or
comprising the cellular material obtained by carrying out the method described in accordance with any one of the variations with reference to the second aspect of the disclosure.

Said device may be selected from: a syringe comprising at least one reservoir receiving a predetermined volume of hydrogel to be injected; a dressing that is capable of delivering at least one functional agent and/or of draining the wound, and a patch that is capable of delivering at least one functional agent such as nicotine.

In particular, said functional agent is a bioactive agent.

In a fourth aspect, the present disclosure provides a device for carrying out the method in accordance with any one of the variations of the first aspect of the disclosure for the production of a hydrogel, the device comprising a first syringe receiving the mixture comprising at least the powders (A) and (B) obtained from the step (ii) and a second syringe receiving a predetermined volume of an acidified aqueous medium including at least one compound (C) comprising at least one unit of a hexose or a unit derived from a hexose, and/or at least one phosphate of said compound (C), said device including means for placing the first and second syringe in fluid communication, in a manner such as to allow the acidified aqueous mixture including at least one compound (C) comprising at least one unit of a hexose or a unit derived from a hexose, and/or at least one phosphate of said compound (C) to be combined with said mixture comprising at least the powders (A) and (B).

Said means for fluid communication may optionally be detachable from the first syringe and the second syringe; they may be detachable.

The first and second syringes may be in fluid communication at their injection ends via means for fluid communication (for example Lueur type fittings), which allow the acidified aqueous medium including at least the compound (C) to be introduced into the first syringe with the aid of the piston of the second syringe, and vice versa via the piston of the first syringe.

The pistons are actuated multiple times until a hydrogel is formed; the shear that is generated promotes dissolution of the chitosan powder and the ionic interactions with the anionic polymer in order to cause a stable, firm hydrogel to be formed.

In accordance with a fifth aspect, the present disclosure provides a hydrogel that is susceptible of being obtained by carrying out the production method in accordance with any one of the variations described with reference to the first aspect of the disclosure, the hydrogel may comprise:

a cyclodextrin polymer (A) obtained by a reaction for polymerizing a mixture comprising at least one cyclodextrin and/or at least one cyclodextrin derivative and/or at least one inclusion complex of cyclodextrin and/or at least one inclusion complex of a cyclodextrin derivative, with at least one (poly)carboxylic acid and/or its corresponding (poly)carboxylic acid anhydride (A1); or at least one pyrophosphate (A2); or at least epichlorhydrin, the polymer obtained then undergoing a carboxymethylation step in a manner such as to graft carboxylic acid functions (—COOH) (A3); and the chitosan (B) including amine functions ($NH_2$).

The cyclodextrin polymer may belong to the family (A1).

In a variation, the anionic polymer (A) includes carboxylic acid functions (—COOH).

In a variation, the anionic polymer (A) includes at least 3 mmoles/g of carboxylic acid functions (COOH).

The variations and definitions described above with reference to any one of aspects one to four and characterizing the hydrogel apply independently to the hydrogel in accordance with a fifth aspect of the disclosure.

DETAILED DESCRIPTION OF THE DRAWINGS

FIGS. 1A and 1B show a hydrogel that has been obtained by a method that differs from the method of the disclosure for producing a hydrogel;

FIGS. 2A and 2B show a hydrogel obtained by carrying out the production method;

Figure 7:
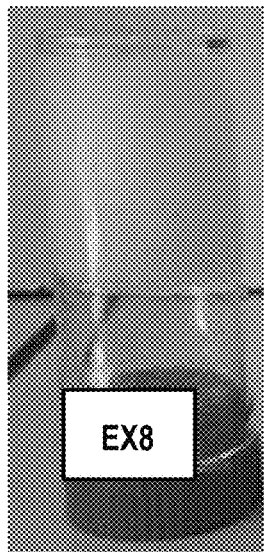
Figure 7:
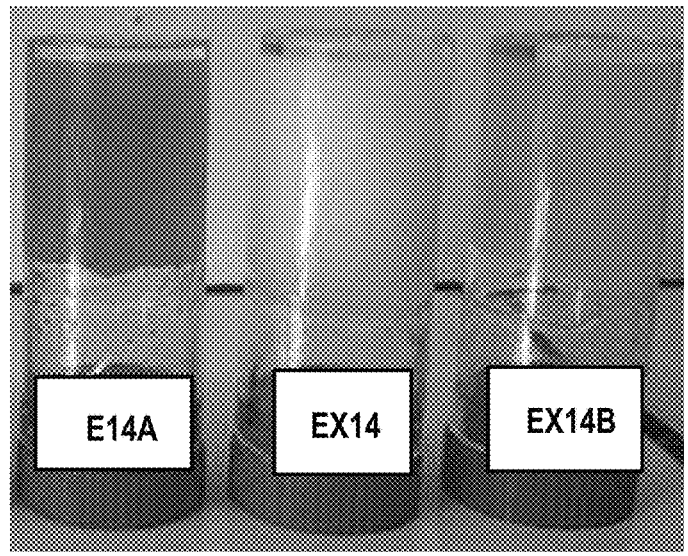
Figure 8:
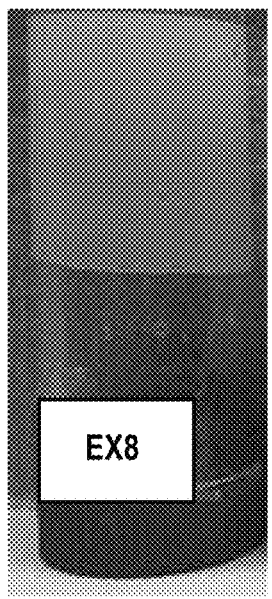
Figure 8:
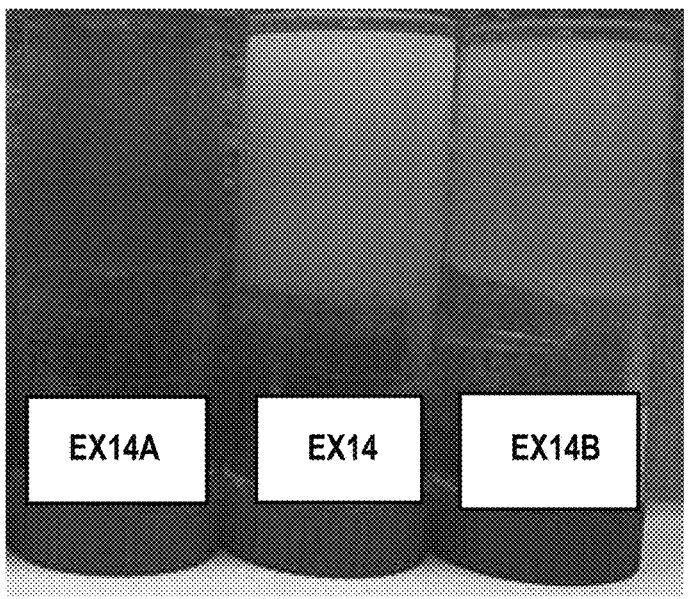

FIGS. 7 and 8 are photographs showing hydrogels of the disclosure, respectively 1 h and 24 h after they have been formed.

DETAILED DESCRIPTION OF THE DISCLOSURE

The present disclosure can be better understood from the following examples, which are non-limiting in nature.

The following compounds were used:

chitosan powder (CHT1): "Chitosan—Medium molecular weight" (Medium Mw: 431 000 g/mol) sold by Sigma Aldrich, CAS number: 9012-76-4, in the form of a powder, the viscosity was 563.00 centipoise (cps) at a concentration of 1% in 1% acetic acid, the degree of deacetylation was greater than or equal to 75%, especially approximately 75%.

chitosan powder (CHT2): "Chitosan—Low molecular weight" (LowMw: 39 000 g/mol) sold by Sigma Aldrich, CAS number: 9012-76-4, in the form of a powder and/or granules, the viscosity was 96 cps at a concentration of 1% in 1% acetic acid, the degree of deacetylation was greater than or equal to 75%.

chitosan powder (CHT3): "Chitosan—High molecular weight" (HighMw: 1 250 000 g/mol) sold by BioResources, CAS number: 9012-76-4, in the form of a powder and/or granules, the degree of deacetylation was greater than or equal to 75%.

cyclodextrin polymer: the polymer was synthesized as follows: 400 g of β-cyclodextrin (Kleptose®, Roquette Frères, Lestrem, France), 400 g of citric acid CAS 77-92-9, Sigma Aldrich, Saint Quentin Fallavier, France), and 120 g of sodium hypophosphite (Sigma Aldrich, Saint Quentin Fallavier, France) were dissolved in 2 liters of an aqueous solution (distilled water). The water of this aqueous solution was then evaporated to dryness under vacuum at 60° C. under 58 mm of mercury in a rotary evaporator for a time sufficient to obtain a solid mixture. The evaporated solid residue was then heated under vacuum at 140° C. for 120 minutes. Next, the solid mixture was taken up into suspension in 2 liters of distilled water. This suspension was filtered through a glass frit. The insoluble polymer was recovered in the filter and was washed with copious amounts of water, then dried at ambient temperature for one week (it could also have been possible, for example, for drying to have been carried out in a ventilated oven at 60° C. for 24 h). The filtrate comprising the soluble polymer was dialyzed on a 6000-8000 Dalton membrane for 5 days, then the dialyzed solution was concentrated using a rotary evaporator. The purified filter was frozen then freeze dried, in this case with the aid of a Christ freeze dryer, model alpha 1-2/LD, at a temperature of −63° C. under a vacuum of 0.06 millibars (mbar), for a time that was sufficient to obtain a solid in the powder form. As an alternative to freeze drying, the purified filtrate could also have been atomized, for example with the aid of a Büchi B-290 atomizer.

71 g of soluble cyclodextrin polymer (CDs1) and 320 g of insoluble cyclodextrin polymer (Cdi1) were obtained.

poly(acrylic) acid (PAA): product code (323667-250G) Mw=1800 and Mw=450 000 supplied by Sigma Aldrich® sodium alginate: product code (180947-500G), batch (09611DD), Sigma Aldrich® pectin from apple (poly-D-galacturonic acid methyl ester): product code (75282-500G), batch (BCBG 4396V), Sigma Aldrich® lactic acid: CAS number 50-21-5, comprising between 85% and 90% by weight of lactic acid relative to the total volume of the solution, ACS reagent grade, Sigma Aldrich®.

I—Description of Operating Mode for Measuring the IEC (Ion Exchange Capacity) of the Cyclodextrin Polymer (Cds1 or Cdi1), i.e. Measurement of the Number of Carboxylic Acid Functions (—COOH) in mmoles Per Gram of Cyclodextrin Polymer 100 mg of polymer (CDs1 or Cdi1) was dissolved in 100 milliliters (mL) of 0.1 M NaCl solution then measured with standard 0.1 M sodium hydroxide in the presence of phenolphthalein as a colored indicator. The normal IEC is approximately 4 mmol per gram of polymer (CDs1 or Cdi1); this is quite close to that for chitosan, which has approximately 5 mmol of amine functions per gram (for a degree of deacetylation of approximately 80%). The gelling phenomenon is linked to the proximity of the IECs for chitosan and for the cyclodextrin polymer (in the family (A1)) and is related to the proportions of chitosan and cyclodextrin polymer brought together to form the gel.

II—Examples of the Preparation of a Hydrogel of the Disclosure and Comparative Examples The proportions marked $_{w/w}$ represent the ratio of the weight of the added component to the total weight of the hydrogel, and thus obtained from the fourth step or from step (v) of the method of the disclosure.

Example 1

0.04 g of chitosan (CHT1) (2%$_{w/w}$) and 0.05 g (2.5%$_{w/w}$) of cyclodextrin polymer (CDs1) were co-milled in a mortar for 1 minute. The powder obtained was taken up into suspension in 1.89 g of ultrapure water then vortex mixed for 15 seconds (the instantaneous pH of the solution was 3.5, which rose to 4.1). 0.02 g of a glacial acetic acid solution was then added to the suspension (the pH dropped to 3.2 during the addition of the acid then rose again to above 5) that was vortex mixed for 20 seconds. A compact gel was obtained after the first seconds of stirring. The hydrogel obtained comprised 89% of water.

Example 2

0.04 g (2%$_{w/w}$) of chitosan (CHT1) and 0.06 g (3%$_{w/w}$) of cyclodextrin polymer (CDs1) were co-milled in a mortar for 1 minute. The powder obtained was taken up into suspension in 1.88 g of ultrapure water then vortex mixed for 15 seconds. 0.02 g of a glacial acetic acid solution was then added to the suspension that was vortex mixed for 20 seconds. A compact gel was obtained after the first seconds of stirring. The hydrogel obtained comprised 72% of water.

Example 3

0.04 g (2%$_{w/w}$) of chitosan (CHT1) and 0.20 g (10%$_{w/w}$) of cyclodextrin polymer (CDs1) were co-milled in a mortar for 1 minute. The powder obtained was taken up into suspension in 1.74 g of ultrapure water then vortex mixed for 15 seconds. 0.02 g of a glacial acetic acid solution was then added to the suspension that was vortex mixed for 20 seconds. A compact gel was obtained after the first seconds of stirring. The hydrogel obtained comprised 60% of water.

Example 4

0.05 g (2.5%$_{w/w}$) of chitosan (CHT1) and 0.06 g (3%$_{w/w}$) of cyclodextrin polymer (CDs1) were co-milled in a mortar for 1 minute. The powder obtained was taken up into suspension in 1.87 g of ultrapure water then vortex mixed for 15 seconds. 0.02 g of a glacial acetic acid solution was then added to the suspension that was vortex mixed for 20 seconds. A compact gel was obtained after the first seconds of stirring. The hydrogel obtained comprised 93% of water.

Example 5

0.02 g (1%$_{w/w}$) of chitosan (CHT1) and 0.04 g (2%$_{w/w}$) of cyclodextrin polymer (CDs1) were co-milled in a mortar for 1 minute. The powder obtained was taken up into suspension in 1.92 g of ultrapure water then vortex mixed for 15 seconds. 0.02 g of a 1% acetic acid solution was then added to the suspension that was vortex mixed for 20 seconds. The gel obtained was not compact and had a tendency to flow slowly.

Example 6

0.06 g (3%$_{w/w}$) of chitosan (CHT1) and 0.04 g (2%$_{w/w}$) of cyclodextrin copolymer (CDs1) were co-milled in a mortar for 1 minute. The powder obtained was taken up into suspension in 1.88 g of ultrapure water then vortex mixed for 15 seconds. 0.02 g of a 1% acetic acid solution was then added to the suspension that was vortex mixed for 20 seconds. The gel obtained during the first seconds of stirring was very compact, did not flow, and was capable of being molded.

Example 7

0.04 g (2%$_{w/w}$) of chitosan (CHT1) and 0.02 g (1%$_{w/w}$) of cyclodextrin polymer (CDs1) were co-milled in a mortar for 1 minute. The powder obtained was taken up into suspension in 1.92 g of ultrapure water then vortex mixed for 15 seconds. 0.02 g of a 1% acetic acid solution was then added to the suspension that was vortex mixed for 20 seconds. The gel obtained had a tendency to flow.

Example 8

0.06 g of chitosan (CHT1) (3%$_{w/w}$) and 0.06 g (3%$_{w/w}$) of cyclodextrin polymer (CDs1) were co-milled in a mortar for 1 minute. The powder obtained was taken up into suspension in 1.86 g of ultrapure water then vortex mixed for 15 seconds. 0.02 g of a glacial acetic acid solution was then added to the suspension that was vortex mixed for 20 seconds. A compact gel was obtained after the first seconds of stirring; it was homogeneous and did not flow under gravity.

Example 9

0.06 g of chitosan (CHT1) (3%$_{w/w}$) and 0.1 g (5%$_{w/w}$) of cyclodextrin polymer (CDs1) were co-milled in a mortar for 1 minute. The powder obtained was taken up into suspension in 1.82 g of ultrapure water then vortex mixed for 15 seconds. 0.02 g of a glacial acetic acid solution was then added to the suspension that was vortex mixed for 20 seconds. A compact gel was obtained after the first seconds of stirring; it was homogeneous and did not flow under gravity.

Example 10 identical to Example 8, with the exception that the chitosan was that with reference CHT2.

Example 11 identical to Example 8, with the exception that the chitosan was that with reference CHT3.

For Examples 10 and 11, the hydrogel obtained was firm, compact, and homogeneous. It did not flow if upturned.

Example 12 identical to Example 8, with the exception that the quantity of chitosan was 3%$_{w/w}$ and the quantity of cyclodextrin polymer (CDs1) was 10%$_{w/w}$. The hydrogel obtained was firm and compact but more viscous, and thicker than the other hydrogels exemplified in the disclosure.

Comparative Example 13 identical to Example 8, with the exception that the cyclodextrin polymer (CDs1) was replaced by a commercial carboxymethyl β-cyclodextrin sodium salt (Aldrich, reference 21906). The hydrogel obtained flowed if it was upturned and it was not firm.

Example 14 identical to Example 8, with the exception that the cyclodextrin polymer (CDs1) was replaced by a polyacrylic acid polymer with a Mw of 1800 (reference given above).

Example 14A identical to Example 8, with the exception that the cyclodextrin polymer (CDs1) was replaced with pectin (reference given above).

Example 14B identical to Example 8, with the exception that the cyclodextrin polymer (CDs1) was replaced with sodium alginate (reference given above).

FIG. 7 shows the hydrogels of Examples 8, 14, 14A and 14B, one hour after their formation.

FIG. 8 shows the hydrogels of Examples 8, 14, 14A and 14B after 24 h. It should be observed that the hydrogels formed from these polyanions were firm and did not flow even 24 h after their formation.

Example 15 identical to Example 8, with the exception that the chitosan polymer was replaced with a high molecular weight polyacrylic acid polymer (Mw: 450 000, reference given above).

The hydrogels of Examples 14 and 15 obtained were firm and did not flow.

Example 16, Control identical to Example 8, with the exception that the cyclodextrin polymer used was synthesized by replacing the β-cyclodextrin with maltodextrin (with a dextrose equivalent value of D19 (19 repeat units), which is sold under the trade mark Glucidex® D19 by Roquette, the linear molecular structure of which does not form a cavity). The gel formed was firm and did not flow.

Comparative Example 17

0.3 g of chitosan (CHT1) (3%$_{w/w}$), milled and sieved through a sieve with 125 µm orifices, was dissolved in a volume of 9.3 mL of ultrapure water (93%$_{w/w}$) to which 0.1 mL of glacial acetic acid had been added (1%$_{w/w}$), it was all mixed at approximately 10 000 revolutions per minute (rpm) with the aid of an Ultra Turrax® type homogenizer for one minute. Next, 0.3 g of cyclodextrin polymer (CDs1 (3%$_{w/w}$), also milled and sieved through a sieve with 125 µm orifices, was added to the acidic chitosan solution (CHT1); the solution was then mixed at approximately 10 000 rpm with the aid of an Ultra Turrax® type homogenizer for one minute. The gelling time measured from the values for G' and G" was 5 days. The gel formed was "liquid", had lumps, was not homogeneous and was not suitable for molding (it flowed under the action of gravity). Adding the anionic polymer (CDs1) to an acidic chitosan solution thus did not allow a firm and compact hydrogel with a self-sustaining shape to be formed. The hydrogel obtained is shown in FIGS. 1A and 1B. It should be noted that in the pot in which it was synthesized in FIG. 1A, the hydrogel flowed over the walls, and thus was not firm. In FIG. 1B, the hydrogel did not retain the shape of a rope which it was given when it was deposited onto a horizontal surface with the aid of a syringe.

Comparative Example 18

0.3 g of chitosan powder (CHT1) (3%$_{w/w}$), not sieved and not milled, and 0.3 g of cyclodextrin polymer powder (CDs1) (3%$_{w/w}$), not sieved and not milled, were dry co-milled in order to reduce their granulometry and to mix them. The mixture of co-milled powders was added to 9.3 mL of ultrapure water (93%$_{w/w}$), the aqueous solution obtained was then vortex mixed for 20 seconds, then 0.1 mL (1%$_{v/v}$) of a glacial acetic acid solution was added. The gelling time measured from the values for G' and G" was more than two and a half hours. The firmness of the hydrogel was correct, but it had lumps.

Comparative Example 19

0.3 g of chitosan powder (CHT1) (3%$_{w/w}$), milled and sieved over a sieve with 125 µm orifices, and 0.3 g of cyclodextrin copolymer powder (CDs1) (3%$_{w/w}$), milled and sieved over a sieve with 125 µm orifices, were co-milled. The mixture of co-milled powders was suspended in 9.3 mL of ultrapure water (93%$_{w/w}$), with stirring at approximately 10 000 rpm with the aid of an Ultra-Turrax® homogenizer for 20 seconds. Next, 0.1 mL (1%$_{v/v}$) of a glacial acetic acid solution was added to the suspension that was mixed with stirring at approximately 10 000 rpm, with the aid of an Ultra-Turrax® homogenizer for 20 seconds. The gelling time measured from the values for G' and G" was more than 2 h30. The gel formed had a good texture, was smooth, homogeneous and firm, i.e. it did not flow under the action of gravity, and was capable of being molded into a predetermined shape. This hydrogel is shown in FIGS. 2A and 2B. It can be seen in FIG. 2A that the hydrogel did not flow onto the walls of the pot in which it had been produced after it was upturned and that it was quite firm. In FIG. 2B, it can be seen that the hydrogel retained its rope shape with which it had been endowed when it came out of a syringe. It can also be seen that it is homogeneous, smooth and did not flow.

The gelling times measured for Examples 17, 18 and 19 were obtained from the graphs for the elastic and viscous moduli G' and G" established as a function of time, with a stress of 100%, a gamma amplitude of 100%, an angular frequency omega of 10 per second (s$^{-1}$) at a temperature of 25° C. using a dynamic mechanical spectrometer such as those sold by Anton Paar.

Example 20

0.3 g of chitosan (CHT1) (3%$_{w/w}$), 0.3 g (3%$_{w/w}$) of cyclodextrin polymer (CDs1) and 0.3 g of hydroxyapatite (3%$_{w/w}$), i.e. 33.3% of the total dry weight of the mixture of powders, were co-milled in a mortar for 1 minute. The mixture of powders obtained was suspended in 9 mL of ultrapure water then vortex mixed for 15 seconds. 0.01 mL (0.1%$_{w/w}$) of a glacial acetic acid solution was then added to the suspension that was vortex mixed for 45 seconds. A compact, homogeneous gel which did not flow under the effect of gravity was obtained.

Examples with an Aqueous Medium Comprising Glucose

Example 27

0.3 g of chitosan (CHT1) (3%$_{w/w}$), 0.3 g (3%$_{w/w}$) of cyclodextrin polymer (CDs1) and 0.3 g of hydroxyapatite (3%$_{w/w}$), i.e. 33.3% of the total dry weight of the mixture of powders, were co-milled in a mortar for 1 minute. The mixture of powders obtained was suspended in 9 mL of an aqueous medium comprising 5% by weight of glucose relative to said volume of said aqueous medium, then vortex mixed for 15 seconds. 0.1 mL of a solution of 85% to 90% concentrated lactic acid was then added to the suspension that was vortex mixed for 45 seconds. The gel was injected in the form of a rope using a syringe into DMEM (Dulbecco's Modified Eagle Medium) medium and into a PBS type medium. The rope formed was firm (could be manipulated with the aid of a spatula) and stable (up to an hour after its formation).

Example 28

This example was the same as for Example 27, with the exception that the mixture of powders was produced with the aqueous medium comprising 5% by weight of glucose relative to the volume of said medium, which had already been acidified with lactic acid, using a device comprising a first syringe receiving the mixture of powders and a second syringe comprising said acidified aqueous medium volume comprising glucose and a means for placing said first and second syringes in fluid communication. Said first and second syringes were in fluid communication, thereby allowing the acidified aqueous medium to pass into the mixture of powders and vice versa. This provision generated shear during mixing of the powders and the aqueous medium, thereby promoting the formation of a hydrogel. The gel formed was then injected in the form of a rope with the aid of said device (retaining only the first or second syringe) into a DMEM medium and into a physiological PBS type medium. The firmness and stability of the rope were improved compared with Example 27.

Example 29

This example was the same as for Example 28, with the exception that the lactic acid was replaced by hydrochloric acid (0.036 M). The gel formed was then injected in the form of a rope with the aid of said device into a DMEM medium and into a physiological PBS type medium. The firmness and stability of the rope were improved compared with Example 27, but were inferior to those obtained for Example 28.

III—Production of a Cellular Material of the Disclosure

Example 21

The hydrogel of Example 8 underwent a freeze drying step in order to form a spongy cellular material such as a foam, with the aid of a Christ model alpha 1-2/LD freeze dryer, at a temperature of −63° C., under a vacuum of 0.06 mbar, for at least 24 h. The degree of swelling was 1739.0% in water at ambient temperature after 6 h and 445.0% in PBS (Phosphate Buffer Saline, pH 7.4, 0.1M) at ambient temperature after 6 h ([(moist weight−dry weight)/dry weight]× 100).

Example 22

The hydrogel of Example 9 underwent a freeze drying step in order to form a cellular material with the aid of a Christ model alpha 1-2/LD freeze dryer, at a temperature of −63° C., under a vacuum of 0.06 mbar, for at least 24 h. The degree of swelling was 262.0% in water at ambient temperature after 6 h and 336.0% in PBS (Phosphate Buffer Saline, pH 7.4, 0.3M) at ambient temperature after 6 h ([(moist weight−dry weight)/dry weight]×100).

Example 23

Figure 3:
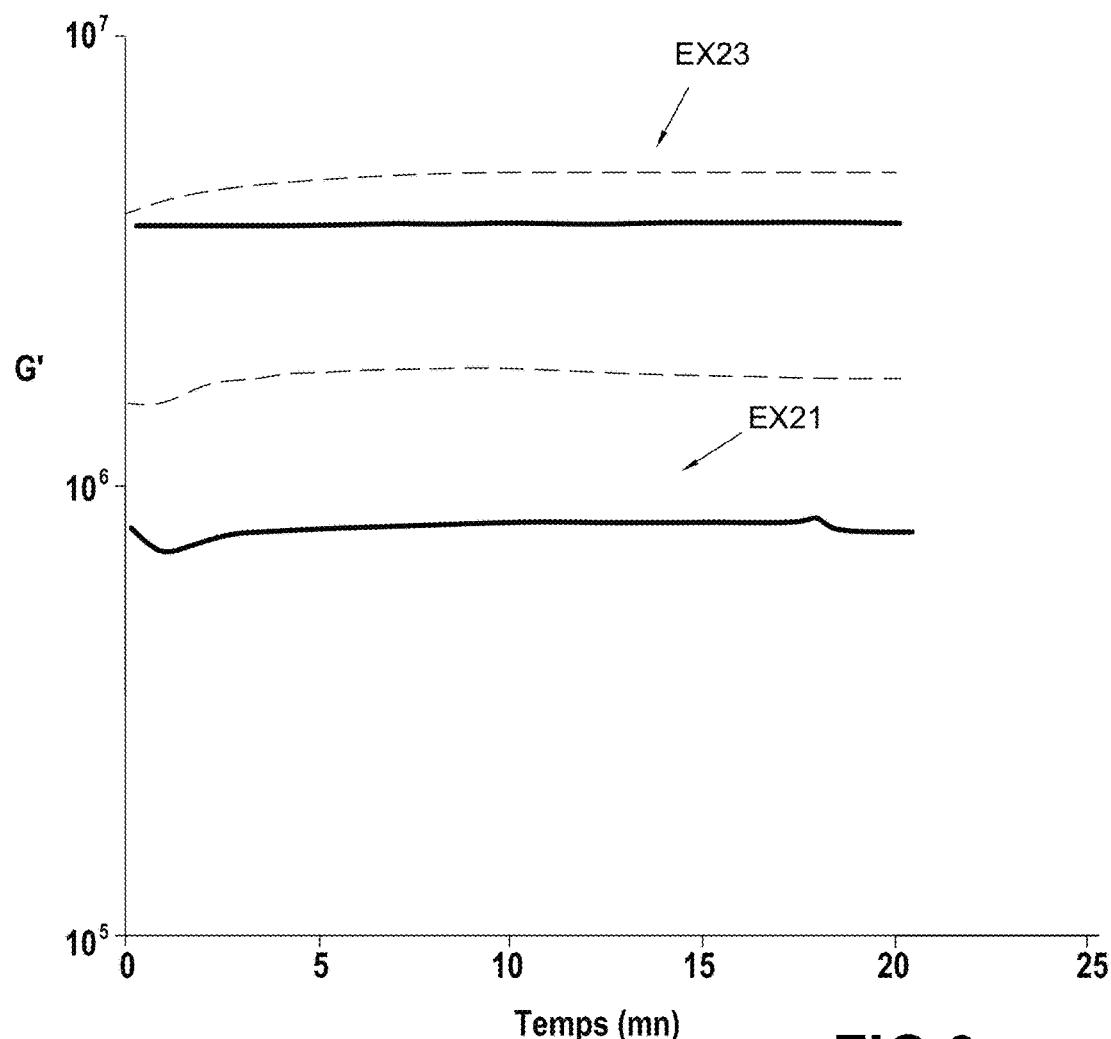
FIG. 3 shows graphs for the elastic moduli G' of the cellular materials of the disclosure.

The cellular material of Example 21 underwent a heat treatment consisting of placing it in a vessel at 140° C. for 1 h. This heat treatment allowed the cellular material to be cross-linked by transforming the ionic bonds into covalent bonds, in particular into amide bonds. It was then observed that the compressive strength, i.e. crush strength, of the cellular material was very significantly improved. This was observed visually by crushing the cellular material of Example 23 between two fingers, whereupon it recovered its shape quasi-instantaneously after deformation was halted, in contrast to the cellular material of Examples 21 or 22. It can be seen in FIG. 3, showing the graphs of the elastic moduli G' for Examples 22 and 21, that the elastic modulus G' of Example 23 which had undergone a heat treatment was substantially higher than the elastic modulus G' of Example 21.

Example 24

Identical to Example 21, with the exception that the hydrogel was synthesized with 10% (w/w) of cyclodextrin polymer (CDs1).

Example 25, Control

The hydrogel of Example 16 underwent a freeze drying step in order to form a cellular material.

Example 26

The hydrogel of Example 20 underwent a freeze drying step in order to form a cellular material with the aid of a Christ model alpha 1-2/LD freeze dryer, at a temperature of −63° C., under a vacuum of 0.06 mbar, for at least 24 h in order to form a cellular material containing hydroxyapatite (33.3% w/w).

IV—Measurement of Cytocompatibility

The cytocompatibility of the hydrogel obtained from Example 8 and the cellular materials from Examples 21 and 22 were tested in accordance with ISO standard 10993-5: 2009—Biological evaluation of medical devices—Part 5—Tests for in vitro cytotoxicity. The cellular viability method was carried out using the alamar blue—extraction test—L132 (ATCC-CCL5) cells method.

The viability measured for Example 8 was 80% after 1 h and 84% after rinsing for 1 h in PBS (Phosphate Buffer Saline, pH 7.4, 0.1M). The viability measured for Example 21 was 91% and 85% for Example 24 after one hour.

The cytotoxicity was measured using the same standard as that described above with cells MC3T3; the control was TCPS (Tissue Culture Polystyrene). A value for Example 28 was obtained that was of the order of 90%, although this value dropped below 60% (approximately 55%) when the aqueous medium did not comprise glucose. When the aqueous medium comprised glucose, the cytotoxicity was substantially improved.

V—Impregnation of Cellular Materials 40 mg of the cellular materials from Examples 21, 22, 24 and 25 were impregnated into an aqueous solution containing 2 mg/mL of ciprofloxacin at ambient temperature with stirring at 250 rpm for 4 h.

Figure 4:
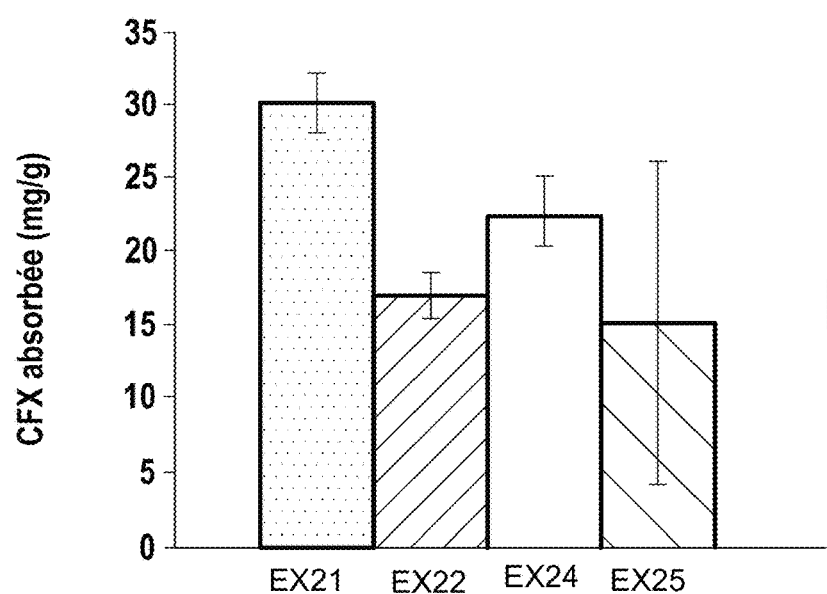
FIG. 4 is a histogram showing, up the ordinate, the quantity of ciprofloxacin (CFX) absorbed in milligrams per gram (mg/g) for the various cellular materials.

The treated cellular materials were placed in a 0.1N sodium hydroxide solution for 24 h at 37° C. in order to extract the adsorbed ciprofloxacin. The solutions obtained were measured using UV spectrophotometry at a wavelength of 271 nm in order to measure the quantity of ciprofloxacin absorbed (mg/g) for each of the cellular materials. The absorption graphs obtained are shown in FIG. 4. The vertical bars on each histogram represent the standard deviations. It should be noted here that the standard deviation for Example 25, which was based on maltodextrin, was higher than that measured for the other examples based on cyclodextrins. This shows that the level of loading with active principle is more random if the dextrin used does not have a hydrophobic cavity and thus does not form an inclusion complex. Examples 21, 22 and 24 indicate that the adsorption capacity of the hydrogels obtained from cyclodextrin polymers varies as a function of the parameters for the preparation of the hydrogel, however the differences are not significant.

Figure 5:
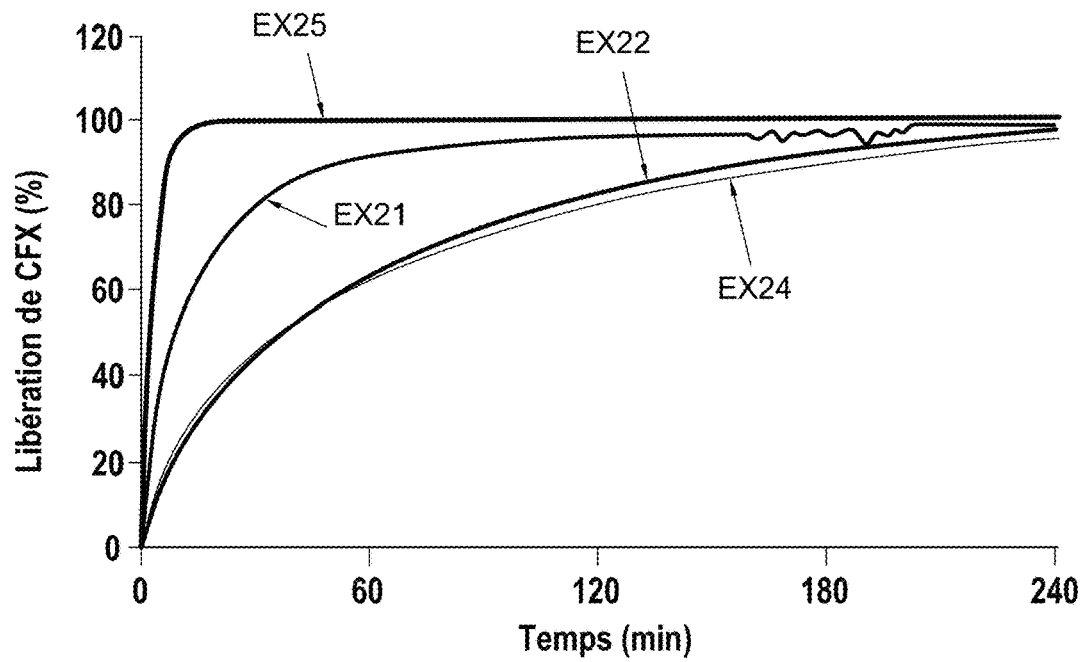
FIG. 5 is a graph showing the graphs for the release of ciprofloxacin as a function of time for various cellular materials, corresponding to those referred to in FIG. 4.

The conditions for release of ciprofloxacin were studied in a closed circuit by injecting a stream of PBS at a temperature of 37° C. at 30 mL/min, starting from a reservoir of 500 mL of PBS, into 30 mg of cellular material impregnated with ciprofloxacin. The stream of PBS leaving the cellular material was then passed into a UV spectrophotometer (wavelength 271 nm) which measured the quantity of ciprofloxacin released; said stream was then redirected to the PBS reservoir. The degree of ciprofloxacin release (%) was measured relative to the absorbed level measured above and shown in FIG. 4. The graphs for the degrees of ciprofloxacin release, shown in FIG. 5, show a very significant difference in the profile for release of ciprofloxacin, which was very rapid for the polymer based on maltodextrin (Example 25) and slowed down for the cellular materials of Examples 21, 22 and 24.

VI—Rheofluidifying Properties of the Hydrogel of the Disclosure (Example 8)

Specifications for the measuring instrument used: rheometer (MCR301-Anton-Paar):

TABLE 1

| | |
|---|---|
| Application | Rheoplus/32 V3.00 21003114-33024 |
| Device | MCR301 SN80167488; FW 3.11; Slot7 |
| Measurement system | PP25-SN17009; Gap[d = 1 mm] |
| Shear rate | 1.308 min/s |
| Shear stress | 327.039 Pa/mNm |
| Correction factor for motor | 1 |
| Time setting | 1 point per min |
| Gamma amplitude ($\gamma$) | 100% (first and second cycle) |
| Angular frequency ($\omega$): | 10 s$^{-1}$ (first cycle); 50 s$^{-1}$ (second cycle) |
| Temperature | 25° C. |

Figure 6:
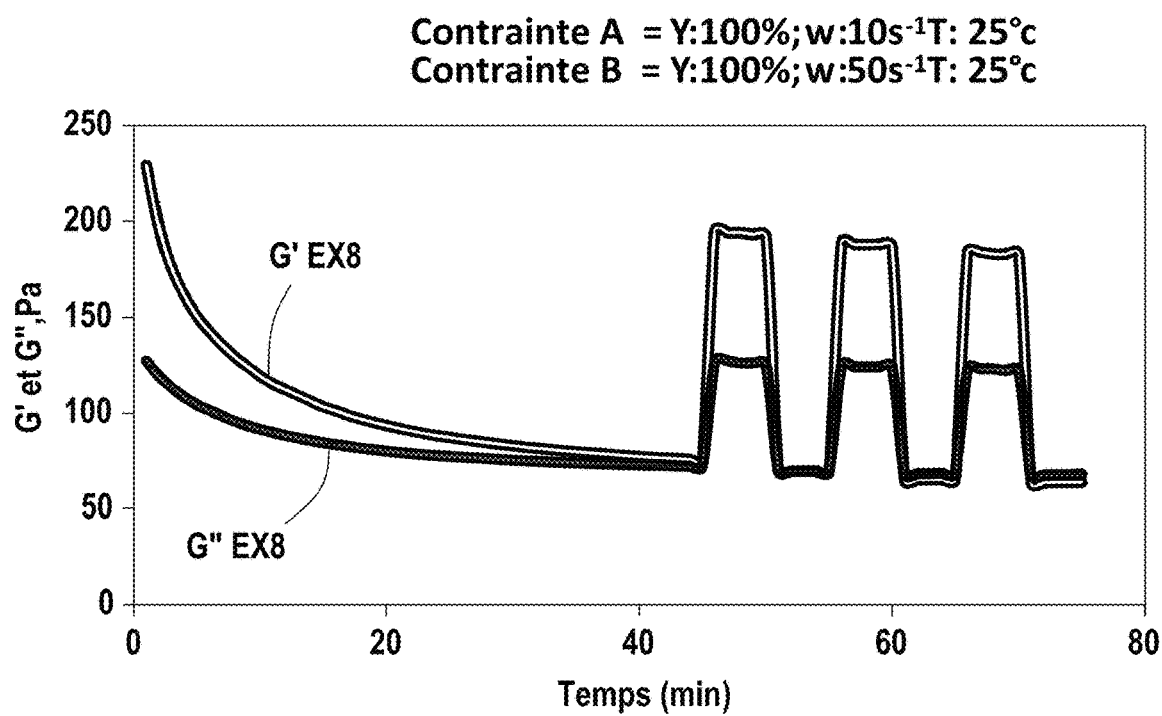
FIG. 6 shows the graphs of the changes in the elastic and viscous moduli G' and G" of a hydrogel example of the disclosure as a function of time (minutes) and for two stresses A and B applied alternately.

The graph shown in FIG. 6 shows the change in the elastic and viscous moduli G' and G" for the hydrogel of Example 8 that has undergone two stress cycles A and B; at t0, G' (230 Pa)>G" (130 Pa) then the stress A applied for 45 minutes caused a reduction in G' until this value merges with that of G". Stopping the stress A followed by immediate application of the stress B caused an instantaneous increase in G' which regained a value close to that at the beginning of the experiment (200 Pa). After 5 minutes under stress B, stress A was applied again and G' regained its minimum value. Alternating stresses A and B over periods of 5 minutes over 3 successive cycles showed a reversible variation in the modulus G', which indicates that the hydrogel has a viscous or elastic type behavior depending on the stress applied. This characteristic is that of a material that has a rheofluidifying behavior (and is therefore thixotropic). By means of this measurement, it has been shown that the hydrogel has the properties necessary to be considered to be injectable, i.e. applicable by means of a syringe: as the piston of the syringe is pushed, the gel fluidifies in the needle or the catheter by the action of shear forces, and once in place in the site for its implantation (bone defect, for example), the hydrogel solidifies again and regains sufficient cohesion to remain in place.

VII—Dynamic Mechanical Thermal Analysis (DMTA) of the Cellular Material of Examples 21 and 23

Specifications of the instrument: Rheometer (MCR301-Anton-Paar).

TABLE 2

| | |
|---|---|
| Application | Rheoplus/32 V3.00 21003114-33024 |
| Device | MCR301 SN80167488; FW 3.11; Slot3; Adj27d |
| Measurement system | RF10-SN11542 |
| Shear rate | 9,1E−03 min/s |
| Shear stress | 142 725.84 Pa/mNm |
| Correction factor for motor | 1 |
| Angle of deflection | 11.5 mrad |
| Time setting | 2 points per min |
| Gamma amplitude | 0.1% |
| Frequency: | 1 Hz |
| Normal force | −1N |
| Temperature | 25° C. |

Characteristics of sample analyzed by DMTA and results of the DMTA:

TABLE 3

| Sample | Thickness (mm) | Length (mm) | Height (mm) | G' (Pa) | G" (Pa) |
|---|---|---|---|---|---|
| Example 21 | 2.49 | 7 | 29 | 1.75E+06 | 1.84E+05 |
| Example 23 | 1.7 | 7 | 29 | 5.11E+06 | 3.79E+05 |

Table 3 above indicates the viscoelastic results for the cellular materials (such as sponges) of Examples 21 and 23. After 20 minutes of analysis at 25° C., it was observed that the elastic modulus (G') was always higher than the viscous modulus (G"), which demonstrates that both cellular materials of Examples 21 and 23 exhibit elastic behavior. It should also be noted that the values for the two moduli G' and G" of Example 23 were much higher than those for Example 21. The heat treatment applied in Example 23 thus improved the mechanical performances of the cellular material. Thus, it may be concluded that during this heat treatment step, the intramolecular behavior has been modified, probably due to the transformations of ionic bonds into covalent bonds, which provides the cellular material of Example 23 with a certain stiffness.

The invention claimed is:

1. A method of producing a hydrogel, comprising the following steps in succession:
    a first step (i) of providing at least one powder of an anionic polymer (A) and at least one chitosan powder (B) comprising amine functions ($-NH_2$);
    a second step (ii) of dry mixing at least the powders (A) and (B) from the first step in order to form a mixture of powders, wherein the powders (A) and (B) are intimately mixed;
    a third step (iii) of suspending the mixture of powders obtained from the second step in an aqueous medium having a pH that can enable the anionic polymer (A) to be dissolved without dissolving the chitosan (B); and
    a fourth step (iv) of adding an acid to the suspension obtained from the third step in order to form the hydrogel;
    wherein the hydrogel is a moldable material and configured to be a self-sustaining shape,
    wherein the degree of deacetylation of the chitosan (B) is higher than or equal to 60% and lower than or equal to 85%,
    wherein the ratio of the weight of the at least one chitosan powder (B) relative to the total weight of the hydrogel is higher than or equal to 1%,
    wherein the ratio of the weight of the at least one anionic polymer powder (A) relative to the total weight of the hydrogel is higher than or equal to 1%, and
    wherein the ratio of the weight of the chitosan powder (B) to the weight of the anionic polymer powder (A) (w/w) is from 0.6 to 1.4.

2. The method according to claim 1, wherein the powder (A) and/or the powder (B) in the first step and/or the mixture of powders comprising at least the powders (A) and (B) in the second step is/are sieved over a sieve with a mesh less than or equal to 500 µm.

3. The method according to claim 1, wherein the anionic polymer comprises functions selected from among the following functions: acid sulfate functions ($-O-S(=O)_2-OH$ or $-SO_4H$), salts of said acid sulfate functions, sulfonic acid functions ($-S(=O)_2-OH$ or $-SO_3H$) salts of said sulfonic acid functions, phosphoric acid functions ($-O-P(=O)_2-OH$ or $-PO_4H$) salts of said phosphoric acid functions, carboxylic acid functions ($-COOH$) salts of said carboxylic acid functions, and combinations thereof.

4. The method according to claim 1, wherein the anionic polymer (A) is a cyclodextrin polymer obtained by a reaction for polymerization of a mixture comprising at least one cyclodextrin and/or at least one cyclodextrin derivative and/or at least one inclusion complex of cyclodextrin and/or at least one inclusion complex of a cyclodextrin derivative, with at least one (poly)carboxylic acid and/or its corresponding (poly)carboxylic acid anhydride (A1).

5. The method according to claim 1, wherein the aqueous medium in step (iii) comprises at least 1% by weight, of at least one compound (C) comprising at least one unit of a hexose or a unit derived from a hexose, and/or of at least one phosphate of said compound (C), relative to the total volume of said aqueous medium.

6. The method according to claim 1, comprising adding at least one mineral filler in the form of a powder to the mixture of powders produced during the second step, wherein the ratio of the weight (g) of mineral filler(s) relative to the total weight of the mixture of powders is higher than or equal to 30%.

7. The method according to claim 6, wherein said mineral filler is a bioceramic selected among: calcium betatriphosphate, calcium carbonate; alumina ($Al_2O_3$), zirconia ($ZrO_2$), glasses, glass ionomer, and titanium dioxide.

8. A method of producing a cellular material, comprising:
    the method of producing the hydrogel according to claim 1; and
    freeze drying the hydrogel to form the cellular material.

9. The method of producing the cellular material according to claim 8, further comprising adding a pore-forming agent in the form of a powder to the mixture of powders during the second step (ii) of the method of producing the hydrogel.

10. The method of producing the cellular material according to claim 8, further comprising heat treating the cellular material at a temperature greater than or equal to 100° C., for at least 5 minutes.

11. The method of producing the cellular material according to claim 8, further comprising impregnating the cellular material in a solution comprising at least one functional agent and/or at least one living cell, wherein said functional agent is selected from a first list (I) comprising anticoagulants, anti-thrombogenics, antimitotics, anti-proliferation agents, anti-adhesion agents, anti-migration agents, cellular adhesion promoters, growth factors, antiparasitic molecules, anti-inflammatory agents, vitamins, hormones, proteins, antifungals, antimicrobial molecules, antiseptics, antibiotics, nicotine, one or more essential oils, or a mixture thereof; and wherein said at least one living cell is selected from a second list (II) comprising human cells, animal cells, or plant cells.

12. A method device for absorbing and draining and/or for releasing a functional agent and/or for supporting living cells, the method comprising:
    the method of producing the hydrogel according to claim 1; and
    preparing a device comprising the hydrogel, wherein the device is selected from: a syringe comprising at least one reservoir receiving a predetermined volume of hydrogel; a dressing which is capable of delivering at least one functional agent and/or capable of draining a wound; a patch that is capable of delivering at least one functional agent.

13. The method according to claim 1, wherein the anionic polymer (A) is a cyclodextrin polymer obtained by a reaction for polymerization of a mixture comprising at least one cyclodextrin and/or at least one cyclodextrin derivative and/or at least one inclusion complex of cyclodextrin and/or at least one inclusion complex of a cyclodextrin derivative, with at least one (poly)carboxylic acid and/or its corresponding (poly)carboxylic acid anhydride (A1); or at least one pyrophosphate (A2).

14. The method according to claim 1, wherein the anionic polymer (A) is a cyclodextrin polymer obtained by a reaction for polymerization of a mixture comprising at least one cyclodextrin and/or at least one cyclodextrin derivative and/or at least one inclusion complex of cyclodextrin and/or at least one inclusion complex of a cyclodextrin derivative, with at least epichlorhydrin, the polymer obtained undergoing a step for carboxyalkylation in a manner such as to graft carboxylic acid functions (A3).

15. A method for absorbing and/or draining and/or releasing a functional agent and/or for supporting at least one living cell, the method comprising:
the method of producing the cellular material according to claim 8; and
preparing a device comprising the cellular material, wherein said device is selected from: a syringe comprising at least one reservoir receiving a predetermined volume of hydrogel to be injected; a dressing that is capable of delivering at least one functional agent and/or of draining the wound, and a patch that is capable of delivering at least one functional agent.

16. A method of producing a hydrogel, comprising:
providing at least one powder of an anionic polymer (A) and at least one chitosan powder (B) comprising amine functions (—NH$_2$);
dry mixing at least the powders (A) and (B) in order to form a mixture of powders;
receiving, in a first syringe, the mixture comprising at least the powders (A) and (B) obtained from the dry mixing;
receiving, in a second syringe, a predetermined volume of an aqueous medium, fluidly communicating the first syringe and the second syringe with one another with a device for suspending the mixture of powders (A) and (B) in the aqueous medium having a pH that can enable the anionic polymer (A) to be dissolved without dissolving the at least one chitosan powder (B);
mixing the aqueous medium with the mixture comprising at least the powders (A) and (B) obtained from the dry mixing; and
adding an acid to the suspension, after fluidly communicating the first syringe and the second syringe with one another, to form the hydrogel.

17. The method according to claim 16, wherein the aqueous medium in the mixing comprises at least 4% by weight of at least one compound (C) comprising at least one unit of a hexose or a unit derived from a hexose, and/or of at least one phosphate of the compound (C), relative to the total volume of the aqueous medium.

* * * * *